(12) United States Patent
Masuyama et al.

(10) Patent No.: US 9,428,485 B2
(45) Date of Patent: Aug. 30, 2016

(54) SALT, PHOTORESIST COMPOSITION AND METHOD FOR PRODUCING PHOTORESIST PATTERN

(75) Inventors: Tatsuro Masuyama, Osaka (JP); Yuichi Mukai, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 13/491,370

(22) Filed: Jun. 7, 2012

(65) Prior Publication Data

US 2012/0315580 A1    Dec. 13, 2012

(30) Foreign Application Priority Data

Jun. 9, 2011 (JP) .................................. 2011-128920
Jul. 29, 2011 (JP) .................................. 2011-166769
Dec. 19, 2011 (JP) .................................. 2011-277196

(51) Int. Cl.

| | | |
|---|---|---|
| *G03F 7/028* | (2006.01) | |
| *C07D 321/10* | (2006.01) | |
| *C07C 309/10* | (2006.01) | |
| *C07C 309/12* | (2006.01) | |
| *C07C 381/12* | (2006.01) | |
| *G03F 7/004* | (2006.01) | |
| *G03F 7/039* | (2006.01) | |
| *G03F 7/11* | (2006.01) | |
| *G03F 7/20* | (2006.01) | |

(52) U.S. Cl.

CPC ........... *C07D 321/10* (2013.01); *C07C 309/10* (2013.01); *C07C 309/12* (2013.01); *C07C 381/12* (2013.01); *G03F 7/0045* (2013.01); *G03F 7/0046* (2013.01); *G03F 7/0397* (2013.01); *G03F 7/11* (2013.01); *G03F 7/2041* (2013.01); *C07C 2101/14* (2013.01); *C07C 2103/74* (2013.01)

(58) Field of Classification Search

USPC ........ 560/14, 149; 562/30; 554/96; 552/112; 568/28; 430/921
See application file for complete search history.

(56) References Cited

U.S. PATENT DOCUMENTS

| | | | |
|---|---|---|---|
| 2002/0102491 A1 | 8/2002 | Kodama et al. | |
| 2008/0166660 A1 | 7/2008 | Takata et al. | |
| 2009/0162788 A1* | 6/2009 | Hada et al. | ................. 430/285.1 |
| 2010/0015552 A1* | 1/2010 | Kawaue et al. | ........... 430/281.1 |
| 2012/0203024 A1* | 8/2012 | Oh et al. | ........................ 560/106 |
| 2012/0237875 A1* | 9/2012 | Asano et al. | ............... 430/283.1 |
| 2012/0264055 A1* | 10/2012 | Ichikawa et al. | ........... 430/280.1 |

FOREIGN PATENT DOCUMENTS

| | | |
|---|---|---|
| JP | 2008-260745 A | 10/2008 |
| JP | 2011095623 A * | 5/2011 |
| WO | WO 2011034176 A1 * | 3/2011 |

OTHER PUBLICATIONS

English Translation of JP2011095623.*

* cited by examiner

*Primary Examiner* — Cynthia H Kelly
*Assistant Examiner* — Anna Malloy
(74) *Attorney, Agent, or Firm* — Birch, Stewart, Kolasch & Birch, LLP

(57) ABSTRACT

A salt represented by formula (I):

$$Z^+ \ ^-O_3S \left( \begin{array}{c} Q^1 \\ | \\ C \\ | \\ Q^2 \end{array} \right)_{m1} O-X^1 \left( O \begin{array}{c} O \\ \| \\ C \\ \end{array} A^1 \right)_{m2}$$ (I)

wherein $Q^1$ and $Q^2$ each independently represent a fluorine atom or a C1-C6 perfluoroalkyl group,
$A^1$ represents a C1-C30 monovalent organic group,
$X^1$ represents a C1-C10 aliphatic hydrocarbon group where a hydrogen atom may be replaced by a hydroxy group,
$m^1$ and $m^2$ independently each represent an integer of 1 to 4, and
$Z^+$ represents an organic cation.

9 Claims, 1 Drawing Sheet

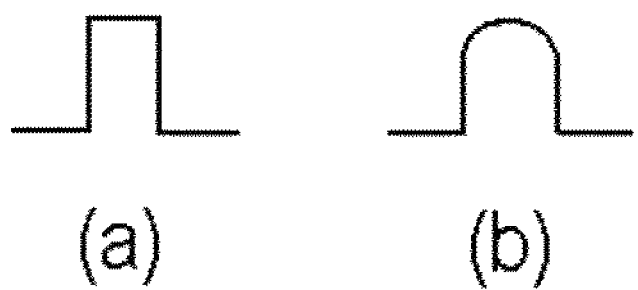

SALT, PHOTORESIST COMPOSITION AND METHOD FOR PRODUCING PHOTORESIST PATTERN

This nonprovisional application claims priority under 35 U.S.C. §119(a) on Patent Application No. 2011-128920 filed in JAPAN on Jun. 9, 2011, No. 2011-166769 filed in JAPAN on Jul. 29, 2011 and No. 2011-277196 filed in JAPAN on Dec. 19, 2011, the entire contents of which are hereby incorporated by reference.

FIELD OF THE INVENTION

The present invention relates to a salt, a photoresist composition and a method for producing a photoresist pattern.

BACKGROUND OF THE INVENTION

A photoresist composition for exposure with ArF, which has actively been studied, is used for semiconductor microfabrication employing a lithography process. Such photoresist composition comprises a resin having an acid-labile group, a solvent and an acid generator comprising a salt.

US2008/166660A mentions a photoresist composition comprising the resin, a salt comprising triphenylsulfonium=4-oxoadamatane-1-yl-oxycarbonyl(difluoro) methanesulfonate.

SUMMARY OF THE INVENTION

The present invention is to provide a photoresist composition suitable for a lithography process.

The present invention relates to the followings:

<1> A salt represented by formula (I):

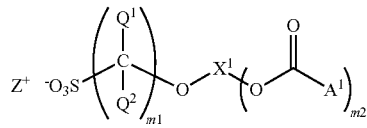

wherein $Q^1$ and $Q^2$ each independently represent a fluorine atom or a C1-C6 perfluoroalkyl group,
$A^1$ represents a C1-C30 monovalent organic group,
$X^1$ represents a C1-C10 aliphatic hydrocarbon group where a hydrogen atom may be replaced by a hydroxy group,
$m^1$ and $m^2$ independently each represent an integer of 1 to 4, and
$Z^+$ represents an organic cation.

<2> The salt according to <1>, wherein $A^1$ represents a C3-C30 alicyclic hydrocarbon group in which a hydrogen atom may be replaced by a hydroxy group or a halogen group and in which a methylene group may be replaced by an oxygen atom, a sulfonyl group or a carbonyl group.

<3> The salt according to <1> or <2>, wherein $A^1$ represents a C3-C30 alicyclic hydrocarbon group in which a hydrogen atom may be replaced by a hydroxy group and in which a methylene group may be replaced by an oxygen atom, a sulfonyl group or a carbonyl group.

<4> The salt according to any one of <1> to <3>, wherein $X^1$ is a C1-C5 aliphatic hydrocarbon group.

<5> The salt according to any one of <1> to <4>, wherein $X^1$ is a C2-C5 aliphatic hydrocarbon group.

<6> The salt according to any one of <1> to <5>, wherein $m^1$ is 2.

<7> The salt according to any one of <1> to <6>, wherein $Z^+$ is an organic cation represented by formula (b2-1-1):

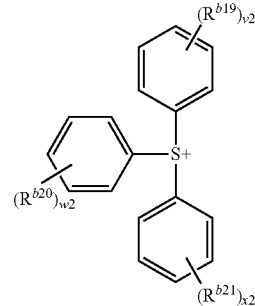

wherein $R^{b19}$, $R^{b20}$ and $R^{b21}$ are independently in each occurrence a halogen atom, a hydroxy group, a C1-C18 alkyl group, a C3-C18 alicyclic hydrocarbon group, or a C1-C12 alkoxy group, and v2, w2 and x2 independently each represent an integer of 0 to 5.

<8> The salt according to <7>, wherein $R^{b19}$, $R^{b20}$ and $R^{b21}$ are a methyl group.

<9> A photoresist composition, which comprises the salt according to any one of <1> to <8> and a resin which is hardly soluble or insoluble but soluble in an aqueous alkali solution by action of an acid.

<10> The photoresist composition according to <9>, which further comprises a resin having a structural unit represented by formula (FI):

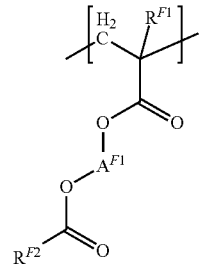

wherein $R^{F1}$ represents a hydrogen atom or a methyl group,
$A^{F1}$ represents a C1-C6 alkanediyl group, and
$R^{F2}$ represents a C1-C10 hydrocarbon group having a fluorine atom.

<11> A process for producing a photoresist pattern comprising the following steps (1) to (5):

(1) a step of applying the photoresist composition according to <9> or <10> on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

The salt of the present invention can give a photoresist composition capable of making a photoresist pattern with less Line width Roughness.

BRIEF DESCRIPTION OF DRAWINGS

FIG. 1 illustrates a cross-section view of photoresist pattern made from the photoresist composition comprising the salt of the present invention.

DESCRIPTION OF PREFERRED EMBODIMENTS

The salt of the present invention is represented by the formula (I). Hereinafter, such salt is sometimes referred to as "SALT (I)".

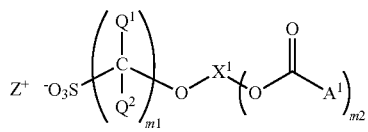

(I)

wherein $Q^1$ and $Q^2$ each independently represent a fluorine atom or a C1-C6 perfluoroalkyl group,
$A^1$ represents a C1-C30 monovalent organic group,
$X^1$ represents a C1-C10 aliphatic hydrocarbon group where a hydrogen atom of which may be replaced by a hydroxy group,
$m^1$ and $m^2$ independently each represent an integer of 1 to 4, and
$Z^+$ represents an organic cation.

Hereinafter, the moiety corresponding to the part except $Z^+$ in formula (I) and having a negative charge is sometimes referred to as "sulfonic acid anion".

The monovalent organic group represented by $A^1$ includes an aliphatic hydrocarbon group, an aromatic hydrocarbon group, and a combined group of an aliphatic hydrocarbon group and an aromatic hydrocarbon group.

Examples of the aliphatic hydrocarbon group include a C1-C30 alkyl group such as a methyl group, an ethyl group, a propyl group, an isopropyl group, a butyl group, a pentyl group, a hexyl group, a heptyl group, an octyl group, a decyl group, dodecyl group, tetradecyl group, a pentadecyl group, a hexadecyl group, a heptadecyl group and an octadecyl group; and
a C3-C30 saturated cyclic hydrocarbon group such as a cyclopropyl group, cyclobutyl group, cyclopentyl group, cyclohexyl group, a cycloheptyl group, a cyclooctyl group, a cyclononyl group, a cyclodecyl group, a norbornyl group, an amadantyl group and an isonorbnornyl group.

Examples of the aromatic hydrocarbon group include a phenyl group, a naphthyl group and an anthryl group.

The combination of an aliphatic hydrocarbon group and an aromatic hydrocarbon group preferably includes combined groups of C1-18 aliphatic hydrocarbon group with the aromatic hydrocarbon group. The organic group represented by $A^1$ is preferably a monovalent aromatic hydrocarbon group which may have a substituent selected from the group consisting of C1-C20 alkyl group, C3-C30 alicyclic hydrocarbon group, an alkoxy group and a hydroxyl group, or a monovalent aliphatic hydrocarbon group which may have a substituent selected from the group consisting of C6-C18 aryl group and a hydroxyl group.

The monovalent aliphatic hydrocarbon group which may have a substituent selected from the group consisting of C6-C18 aryl group and a hydroxyl group preferably includes an alkyl group, specifically C1-C10 alkyl group, such as a methyl group, an ethyl group, a propyl group, a butyl group, a pentyl group, a hexyl group, a heptyl group, an octyl group, a decyl group, a dodecyl group,
a cycloalkyl group, specifically C3-C10 cycloalkyl group, such as cyclopropyl group, cyclobutyl group, cyclopentyl group, cyclohexyl group, a cycloheptyl group, a cyclooctyl group, a cyclononyl group, a cyclodecyl group, a norbornyl group, a 1-amadantyl group, a 2-amadantyl group and an isonorbnornyl group,
an aralkyl group, specifically C7-C11 aralkyl group, such as a benzyl group and naphtylmethyl group, and
a hydroxyalkyl group, specifically C1-C10 hydroxyalkyl group, such as a hydroxymethyl group, an hydroxyethyl group, a hydroxypropyl group, a hydroxybutyl group, a hydroxypentyl group, a hydroxyhexyl group, a hydroxyheptyl group, and a hydroxyoctyl group.

The monovalent aromatic hydrocarbon group which may have a substituent selected from the group consisting of C1-C20 alkyl group, C3-C30 alicyclic hydrocarbon group, an alkoxy group and a hydroxyl group includes
an aryl group, specifically C6-C20 aralkyl group, such as a phenyl group, a naphthyl group, an anthryl group, a biphenyl group, an antlyl group and a phenanthryl group; an alkylaryl group such as p-methylphenyl group, p-butylphenyl group, a tolyl group, a xylyl group, a cumenyl group, a mesityl group, 2,6-diethylphenyl group, and 2-methyl-6-ethylphenyl group;
a hydroxyaryl group, specifically C6-C20 hydroxyaryl group, such as a phenoxy group and a hydroxynaphthyl group; and
an alkoxyaryl group, specifically C7-C24 alkoxyaryl group, such as a methoxyphenyl group, an ethoxyphenyl group, a dimethoxyphenyl group, a methoxynaphthyl group, an ethoxynaphthyl group and dimethoxynaphthyl group.

$A^1$ is preferably a C3-C30 alicyclic hydrocarbon group, more preferably a C6-C20 alicyclic hydrocarbon group.

In the alicyclic hydrocarbon group, preferably a C3-C30 alicyclic hydrocarbon group, represented by $A^1$, a hydrogen atom may be replaced by a hydroxyl group or a halogen atom, preferably by a hydroxyl group, and a methylene group can be replaced by an oxygen atom, sulfonyl group or carbonyl group. The halogen atom includes a fluorine atom, a chlorine atom, an iodine atom or a bromine atom, preferably a fluorine atom.

The alicyclic hydrocarbon group in which a methylene group can be replaced by an oxygen atom, sulfonyl group or carbonyl group includes those represented by the following formulae.

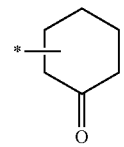

(A12)

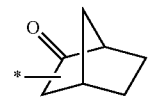

(A13)

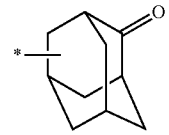

(A14)

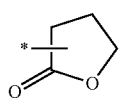 (A15)
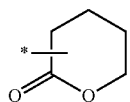 (A16)
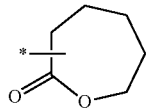 (A17)
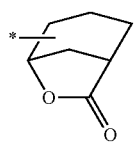 (A18)
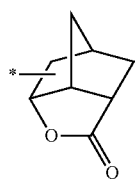 (A19)
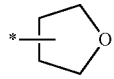 (A20)
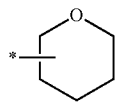 (A21)
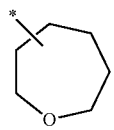 (A22)
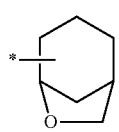 (A23)
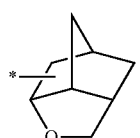 (A24)
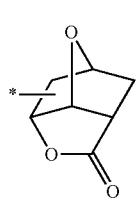 (A25)
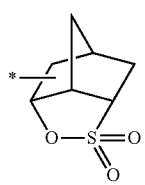 (A26)
Among them, the groups represented by (A14) and (A19) are preferred. Examples of $A^1$ include the following ones.
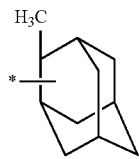 (A27)
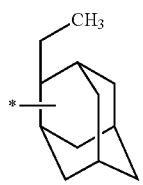 (A28)
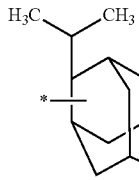 (A29)
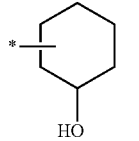 (A30)
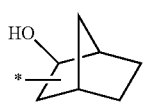 (A31)
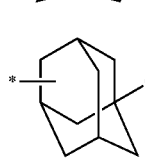 (A32)
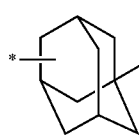 (A33)
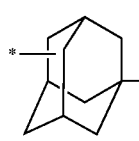 (A34)

-continued

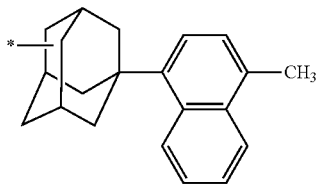
(A35)

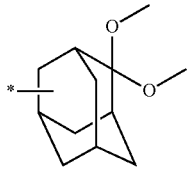
(A36)

(A37)

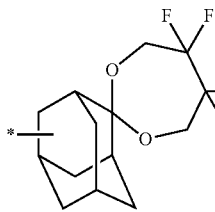
(A38)

(A39)

When $A^1$ represents an alicyclic hydrocarbon group, the alicyclic hydrocarbon group is preferably a cyclohexyl group, an adamantyl group, and the groups represented by formulae (A14), (A19), (A28) and (A32).

$m^1$ and $m^2$ independently each represent an integer of 1 to 4. $m^1$ preferably represents 2. The $m^2$ preferably represents 1 or 2.

The C1-C10 aliphatic hydrocarbon group represented by $X^1$ is $(1+m^2)$-valent group. Herein, "$(1+m^2)$-valent" means the valency of the group is $1+m^2$, where $m^2$ is defined above.

The C1-C10 aliphatic hydrocarbon group represented by $X^1$ includes;

such groups that $m^2$ of hydrogen atom(s) has/have been removed from C1-C10 alkyl groups including a methyl group, an ethyl group, a propyl group, a butyl group, a pentyl group, a hexyl group, a heptyl group, an octyl group, a decyl group;

such groups that $m^2+1$ of hydrogen atoms have been removed from C3-C10 cycloalkyl groups including a cyclopropyl group, a cyclobutyl group, a cyclopentyl group, a cyclohexyl group, a cycloheptyl group, a cyclooctyl group, a cyclononyl group, a norbornyl group, an adamantly group, and a cyclodecyl group; and such groups that $m^2+1$ of hydrogen atom(s) has/have been removed from a combined group of C1-C10 alkyl groups and C3-C10 cycloalkyl groups.

Such groups that $m^2+1$ of hydrogen atom(s) has/have been removed from a combined group of C1-C10 alkyl groups and C3-C10 cycloalkyl groups include groups represented by formulae $(X^1\text{-A})$, $(X^1\text{-B})$ and $(X^1\text{-C})$:

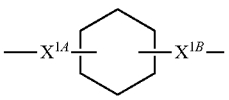
$(X^1\text{-A})$

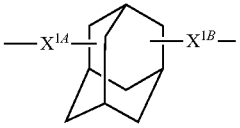
$(X^1\text{-B})$

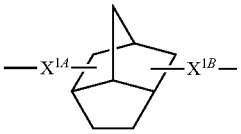
$(X^1\text{-C})$ wherein $X^{1A}$ and $X^{1B}$ each independently represent a C1-C6 alkanediyl group, provided that the total number of carbon atoms is up to 17 in each group, and a methylene group of the alkanediyl group may be replaced by an oxygen atom or a carbonyl group.

The alkanediyl group includes a methylene group, an ethylene group, a propylene group, a butylene group, a pentylene group, a hexylene group.

$X^1$ is preferably C1-C5 aliphatic hydrocarbon group, more preferably a C2-C5 aliphatic hydrocarbon group, still more preferably a C2-C5 alkandiyl group.

The anion sulfonate of SALT (I) preferably includes the moieties represented by formula (a-1-1), formula (a-1-2), formula (a-1-3), formula (a-1-4), formula (a-1-5), formula (a-1-6), formula (a-1-7), formula (a-1-8), formula (a-1-9), formula (a-1-10), formula (a-1-11), formula (a-1-12), formula (a-1-13), formula (a-1-14), formula (a-1-15), formula (a-1-16), formula (a-1-17), formula (a-1-18), formula (a-1-19), formula (a-1-20), formula (a-1-21), formula (a-1-22), formula (a-1-23), formula (a-1-24), formula (a-1-25), formula (a-1-26), formula (a-1-27), formula (a-1-28), formula (a-1-29), formula (a-1-30), formula (a-1-31), formula (a-1-32) or formula (a-1-33). As the anion sulfonate, more preferred are those represented by formula (a-1-3), formula (a-1-4), formula (a-1-5), formula (a-1-6), formula (a-1-7), formula (a-1-8), formula (a-1-10), formula (a-1-13), formula (a-1-14), formula (a-1-15), formula (a-1-23), formula (a-1-24), formula (a-1-25) and formula (a-1-33), and still more preferred are those represented by formula (a-1-5), formula (a-1-7), formula (a-1-13), formula (a-1-23), formula (a-1-24), formula (a-1-25) and formula (a-1-33), and particularly more preferred are those represented by formula (a-1-5), formula (a-1-7), formula (a-1-13), formula (a-1-23), formula (a-1-24), and formula (a-1-25).

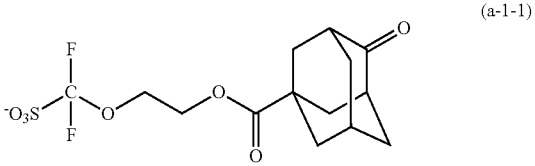
(a-1-1)

-continued
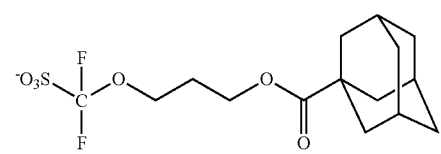
(a-1-2)
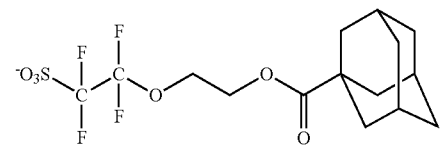
(a-1-3)
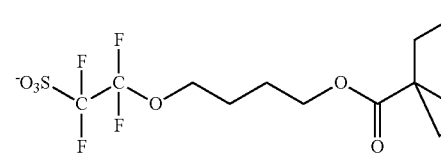
(a-1-4)
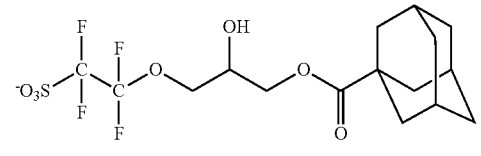
(a-1-5)
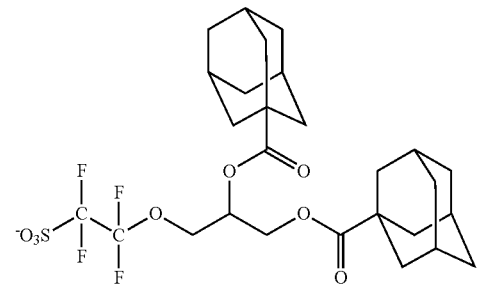
(a-1-6)
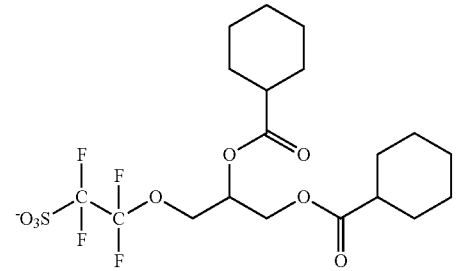
(a-1-7)
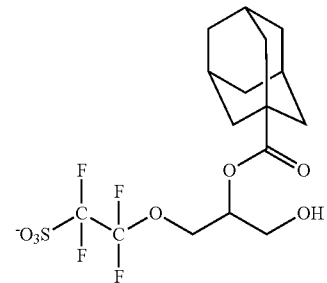
(a-1-8)
-continued
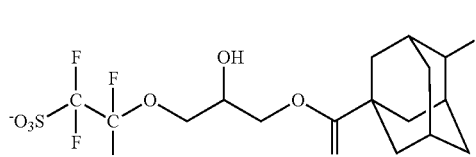
(a-1-9)
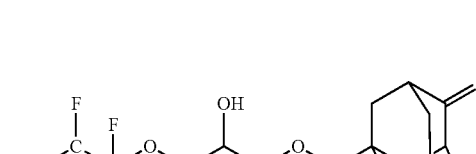
(a-1-10)
(a-1-11)
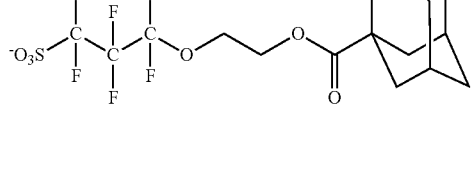
(a-1-12)
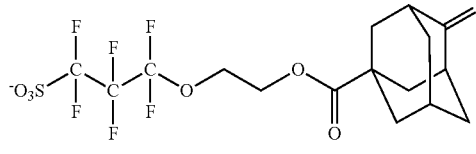
(a-1-13)
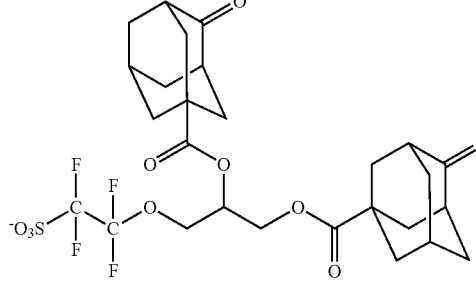
(a-1-14)
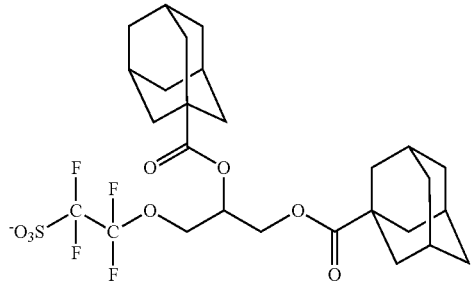

(a-1-15)
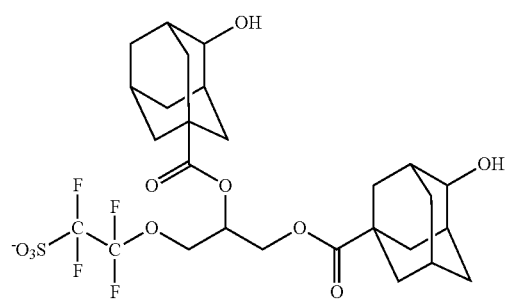
(a-1-16)
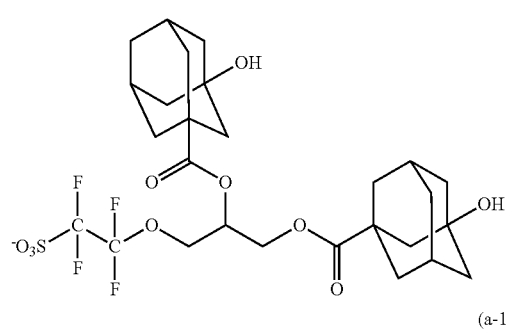
(a-1-17)
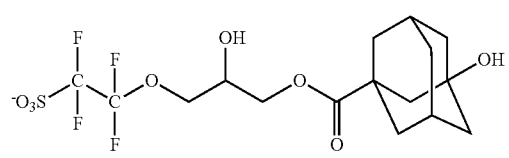
(a-1-18)
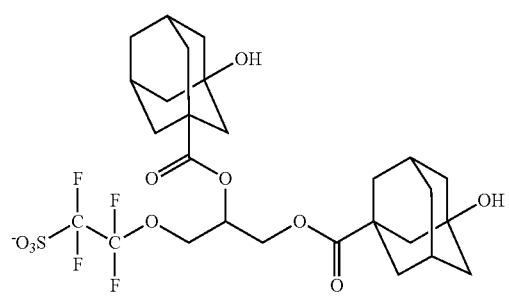
(a-1-19)
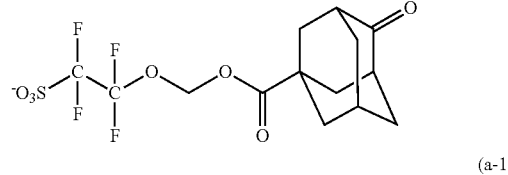
(a-1-20)
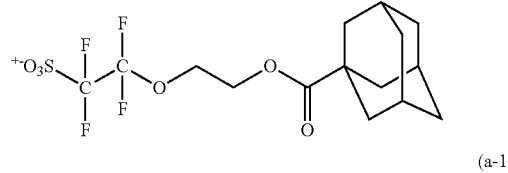
(a-1-21)
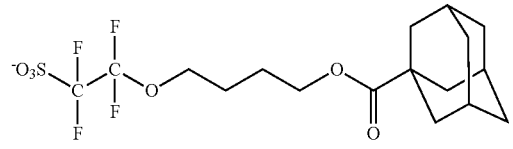
(a-1-22)
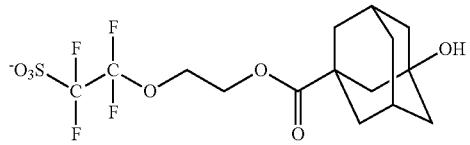
(a-1-23)
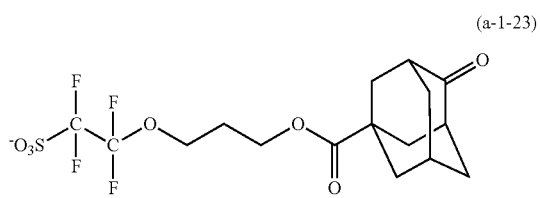
(a-1-24)
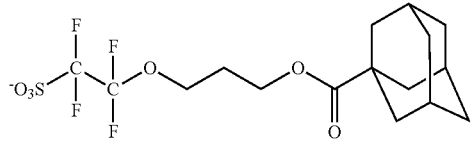
(a-1-25)
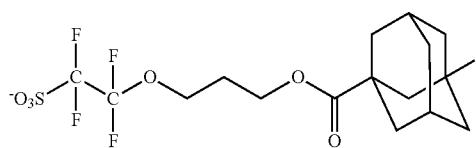
(a-1-26)
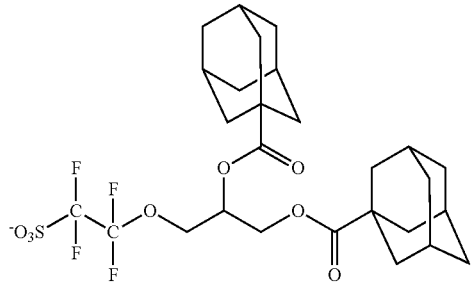
(a-1-27)
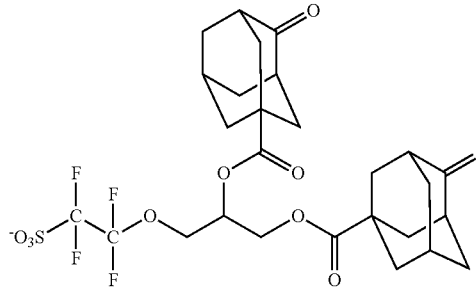

(a-1-28)
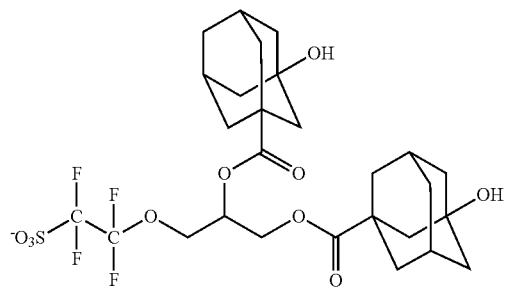

(a-1-29)
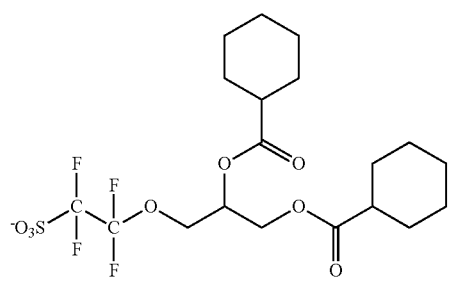

(a-1-33)
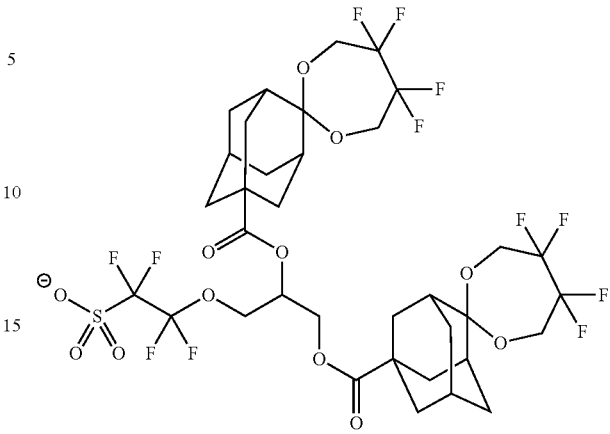

$Z^+$ represents an organic cation.

Examples of the organic cation represented by $Z^+$ include an organic onium cation such as an organic sulfonium cation, an organic iodonium cation, an organic ammonium cation, a benzothiazolium cation and an organic phosphonium cation, and an organic sulfonium cation and an organic iodonium cation are preferable, and an organic cation represented by formulae (b2-1), (b2-2), (b2-3) and (b2-4) is more preferable.

(a-1-30)
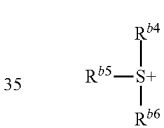

(b2-1)

(a-1-31)

(b2-2)
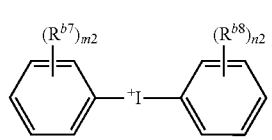

(b2-3)
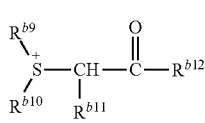

(a-1-32)

(b2-4)
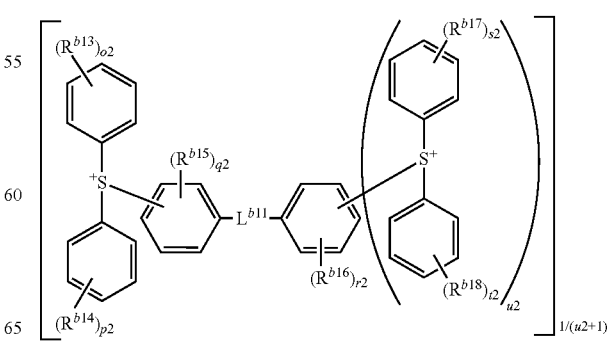

wherein $R^{b4}$, $R^{b5}$ and $R^{b6}$ independently represent a C1-C30 hydrocarbon group,
$R^{b7}$ and $R^{b8}$ are independently in each occurrence a hydroxy group, a C1-C12 alkyl group or a C1-C12 alkoxy group, m2 and n2 independently represents an integer of 0 to 5, $R^{b9}$, $R^{b10}$ and $R^{b11}$ each independently represent an aliphatic hydrocarbon group, or $R^{b9}$ and $R^{b10}$ are bonded each other to form a C2-C10 divalent acyclic hydrocarbon group which forms a 3- to 12-membered ring, preferably 3- to 7-membered ring together with the adjacent —S$^+$—, and one or more —CH$_2$— in the divalent acyclic hydrocarbon group may be replaced by an oxygen atom, sulfur atom or carbonyl group, $R^{b11}$ represents a hydrogen atom, a C1-C18 alkyl group, or a C3-C18 alicyclic hydrocarbon group, or a C6-C18 aromatic hydrocarbon group, $R^{b12}$ represents a C1-C18 hydrocarbon group, or $R^{b11}$ and $R^{b12}$ are bonded each other to form a C2-C10 divalent acyclic hydrocarbon group which forms a 2-oxocycloalkyl group together with the adjacent —CHCO—, and one or more —CH$_2$— in the divalent acyclic hydrocarbon group may be replaced by an oxygen atom, sulfur atom or carbonyl group, $R^{b13}$, $R^{b14}$, $R^{b15}$, $R^{b16}$, $R^{b17}$ and $R^{b18}$ independently represent a hydroxy group, a C1-C12 alkyl group or a C1-C12 alkoxy group, $L^{b11}$ represents a sulfur atom or an oxygen atom, and o2, p2, s2 and t2 each independently represents an integer of 0 to 5,
q2 and r2 each independently represents an integer of 0 to 4, and
u2 represents 0 or 1.

As the hydrocarbon group represented by $R^{b4}$, $R^{b5}$ and $R^{b6}$, preferred are a C1-C18 alkyl group in which a hydrogen atom can be replaced by a hydroxy group, or a C1-C12 alkoxy group, a C6-C18 aromatic hydrocarbon group, a C3-C18 alicyclic hydrocarbon group in which a hydrogen atom can be replaced by a halogen atom, a C2-C4 acyl group or a glycidyloxy group, and a C6-C18 aromatic hydrocarbon group in which a hydrogen atom can be replaced by a halogen atom, a hydroxy group, C3-C18 alicyclic hydrocarbon group, or C1-C12 alkoxy group.

The aliphatic hydrocarbon group represented by $R^{b9}$ or $R^{b10}$ includes a C1-C18, preferably C1-C12, alkyl group and a C3-C18, preferably C4-C12, alicyclic hydrocarbon group.

Preferable examples of the alkyl group represented by $R^{b4}$ to $R^{b6}$ include a methyl group, an ethyl group, a propyl group, an isopropyl group, a butyl group, a sec-butyl group, a tert-butyl group, a pentyl group, a hexyl group, an octyl group, a decyl group, a dodecyl group, a hexadecyl group, a pentadecyl group, a heptadecyl group and an octadecyl group, and more preferable examples thereof include a methyl group, an ethyl group, a propyl group and a butyl group. Preferable examples of the alicyclic hydrocarbon group represented by $R^{b4}$ to $R^{b6}$ include a cyclopropyl group, a cyclobutyl group, a cyclopentyl group, a cyclohexyl group, a cycloheptyl group, a cyclodecyl group, an adamantyl group, a 2-alkyladamantyl-2-yl group, a 1-(adaman-2-yl)alkane-1-yl group and an isobornyl group, and more preferable examples thereof include a cyclopentyl group and a cyclohexyl group. Preferable examples of the aromatic group represented by $R^{b4}$ to $R^{b6}$ include a phenyl group, a naphthyl group and an anthryl group, and a phenyl group is more preferable. Examples of the C1-C12 alkoxy group include a methoxy group, an ethoxy group, a propoxy group, a butoxy group, a pentyloxy group, a hexyloxy group, a heptyloxy group, an octyloxy group, a decyloxy group and a dodecyloxy group. Examples of the halogen atom include a fluorine atom, a chlorine atom, a bromine atom and an iodine atom. Examples of the C2-C4 acyl group include an acetyl group, a propyonyl group and a butyryl group.

Preferable examples of the alkyl group represented by $R^{b7}$ and $R^{b8}$ include a methyl group, an ethyl group, a propyl group, an isopropyl group, a butyl group, a sec-butyl group, a tert-butyl group, a pentyl group, a hexyl group, an octyl group and a 2-ethylhexyl group. Examples of the C1-C12 alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Preferable examples of the alkyl group represented by $R^{b9}$ to $R^{b12}$ include a methyl group, an ethyl group, a propyl group, an isopropyl group, a butyl group, a sec-butyl group, a tert-butyl group, a pentyl group, a hexyl group, an octyl group and a 2-ethylhexyl group. Such alkyl group preferably has 1 to 12 carbon atoms. Preferable examples of the alicyclic hydrocarbon group represented by $R^{b9}$ to $R^{b11}$ include a cyclopropyl group, a cyclobutyl group, a cyclopentyl group, a cyclohexyl group, a cycloheptyl group, a cyclodecyl group, a 2-alkyl-2-adamantyl group, a 1-(1-adamantyl)-1-alkyl group and an isobornyl group.

The alicyclic hydrocarbon group represented by $R^{b9}$ to $R^{b11}$ has preferably 4 to 12 carbon atoms.

Preferable examples of the aromatic group represented by $R^{b12}$ include a phenyl group, 4-methylphenyl group, 4-ethylphenyl group, 4-tert butylphenyl group, 4-cyclohexylphenyl group, 4-methoxyphenyl group, biphenyl group and a naphthyl group, and a phenyl group is more preferable.

Preferable examples of the group in which the alkyl group has been combined with the aromatic hydrocarbon group represented by $R^{b12}$ include an aralkyl group such as benzyl group. Preferable examples of the alkylcarbonyloxy group represented by $R^{b12}$ include a group consisting of an acyl group and an oxygen atom.

Examples of the C3-C12 divalent acyclic hydrocarbon group formed by bonding $R^{b9}$ and $R^{b10}$ include a trimethylene group, a tetramethylene group and a pentamethylene group. Examples of the ring group formed together with the adjacent S$^+$ and the divalent acyclic hydrocarbon group include a thiolan-1-ium ring (tetrahydrothiphenium ring), a thian-1-ium ring and a 1,4-oxathian-4-ium ring. A C3-C7 divalent acyclic hydrocarbon group is preferable.

Examples of the C1-C10 divalent acyclic hydrocarbon group formed by bonding $R^{b11}$ and $R^{b12}$ include a methylene group, an ethylene group, a trimethylene group, a tetramethylene group and a pentamethylene group and examples of the ring group include oxocyclopentane ring, oxocyclohexane ring, oxonorbornane ring and oxoamadantane ring. A C1-C5 divalent acyclic hydrocarbon group is preferable.

Examples of the group in which the alkyl group has been combined with the aromatic hydrocarbon group include typically an aralkyl group, preferably benzyl group. As examples of the organic cations represented by formulae (b2-1) to (b2-4) include organic cations mentioned in JP2010-204646A1.

Among the above-mentioned cations, preferred is the cation represented by the formula (b2-1), more preferred is the cation represented by the formula (b2-1) in which any of $R^{b4}$, $R^{b5}$ and $R^{b6}$ is an aromatic hydrocarbon group, still more preferred is the cation represented by the formula (b2-1-1), especially more preferred is triphenylphosphonium cation or tritolylsulfonium cation.

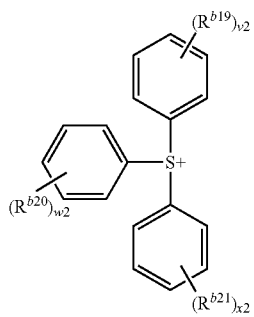
(b2-1-1)

wherein $R^{b19}$, $R^{b20}$ and $R^{b21}$ are independently in each occurrence a halogen atom (preferably a fluorine atom); a hydroxy group; a C1-C18 aliphatic hydrocarbon group in which one or more hydrogen atoms can be replaced by a halogen group, a C2-C4 acyl group, or a grycidyloxy group; or a C1-C12 alkoxy group; and $R^{b19}$ and $R^{b20}$, $R^{b19}$ and $R^{b21}$ or $R^{b20}$ and $R^{b21}$ can be bonded each other to form a ring together with $S^+$, and v2, w2 and x2 independently each represent an integer of 0 to 5. The aliphatic hydrocarbon group of $R^{b19}$, $R^{b20}$ and $R^{b21}$ includes an alkyl group and an alicyclic hydrocarbon group, preferably C1-C12 alkyl group and C4-C18 alicyclic hydrocarbon group.

Each of $R^{b19}$, $R^{b20}$ and $R^{b21}$ is preferably a halogen atom (preferably a fluorine atom), a hydroxy group, a C1-C12 alkyl group and a C1-C12 alkoxy group, and more preferably a halogen atom (preferably a fluorine atom) and a C1-C6 alkyl group.

The v2, w2 and x2 independently each represent 0 or 1.

Preferred examples of SALT (I) include those represented as follow.

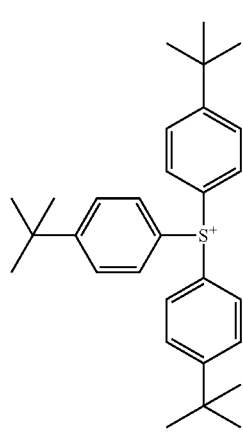
(I-1)

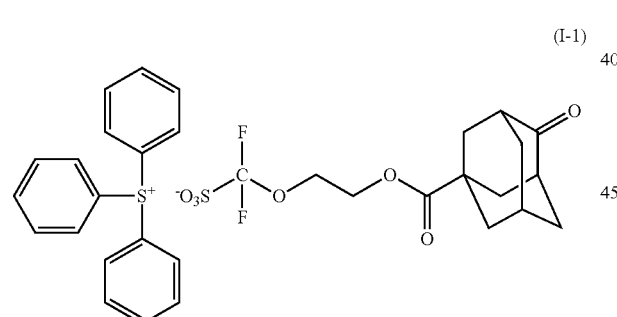
(I-2)

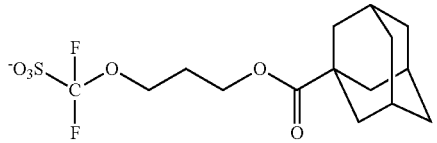

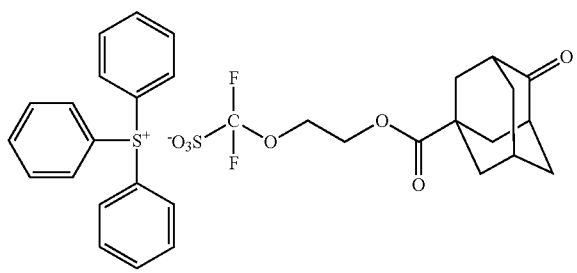
(I-3)

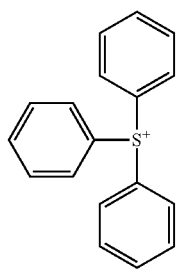
(I-4)

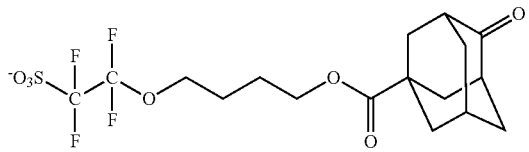

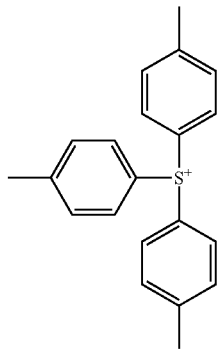
(I-5)

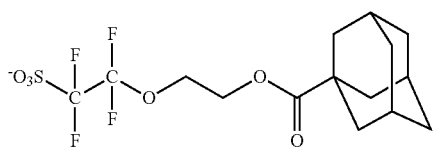

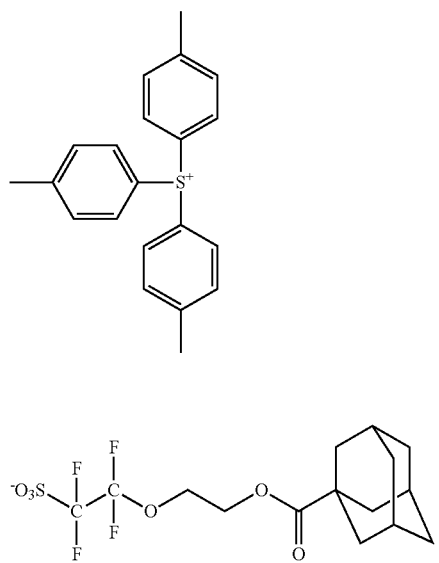
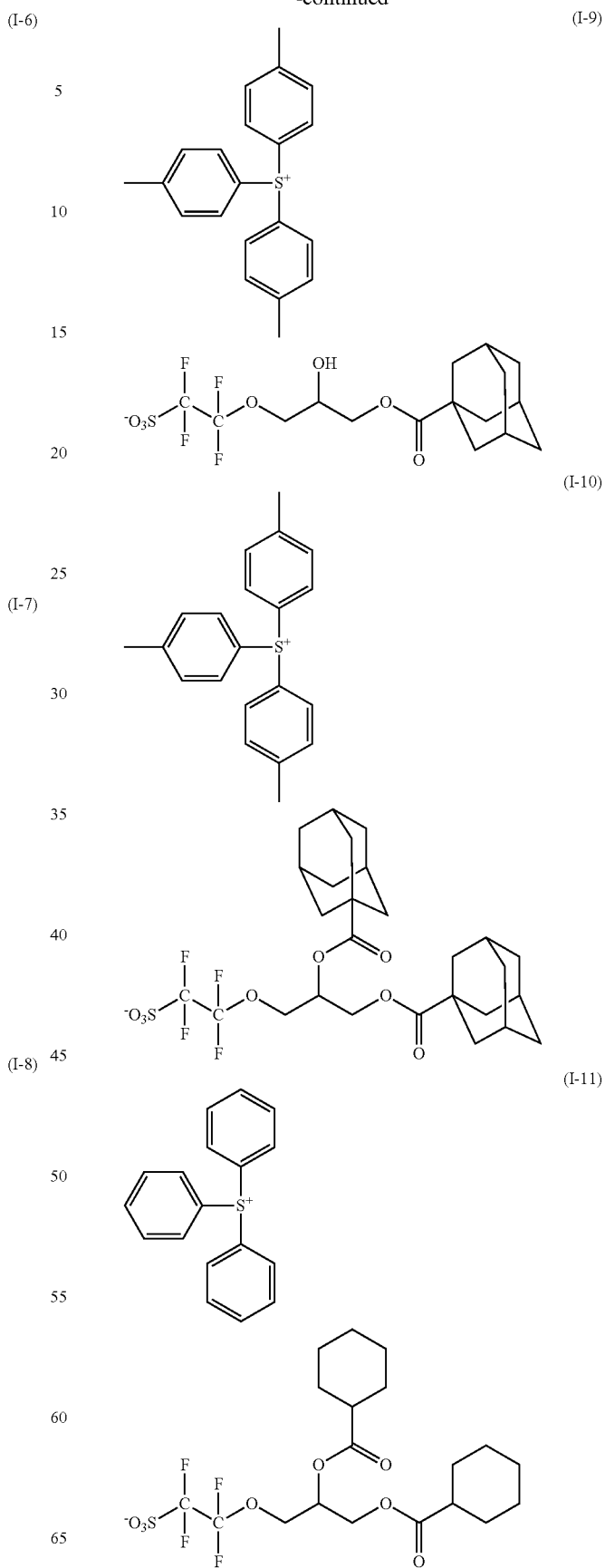

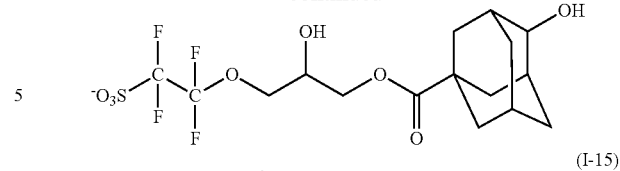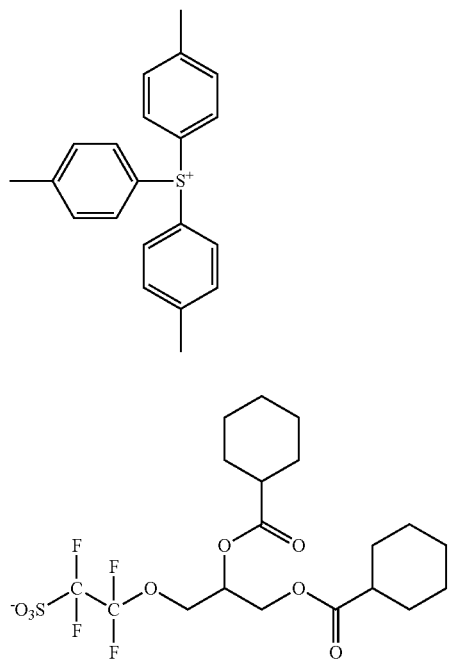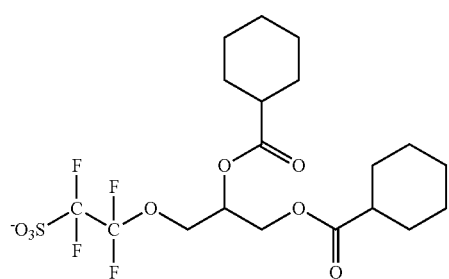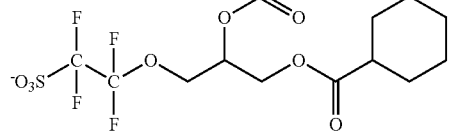

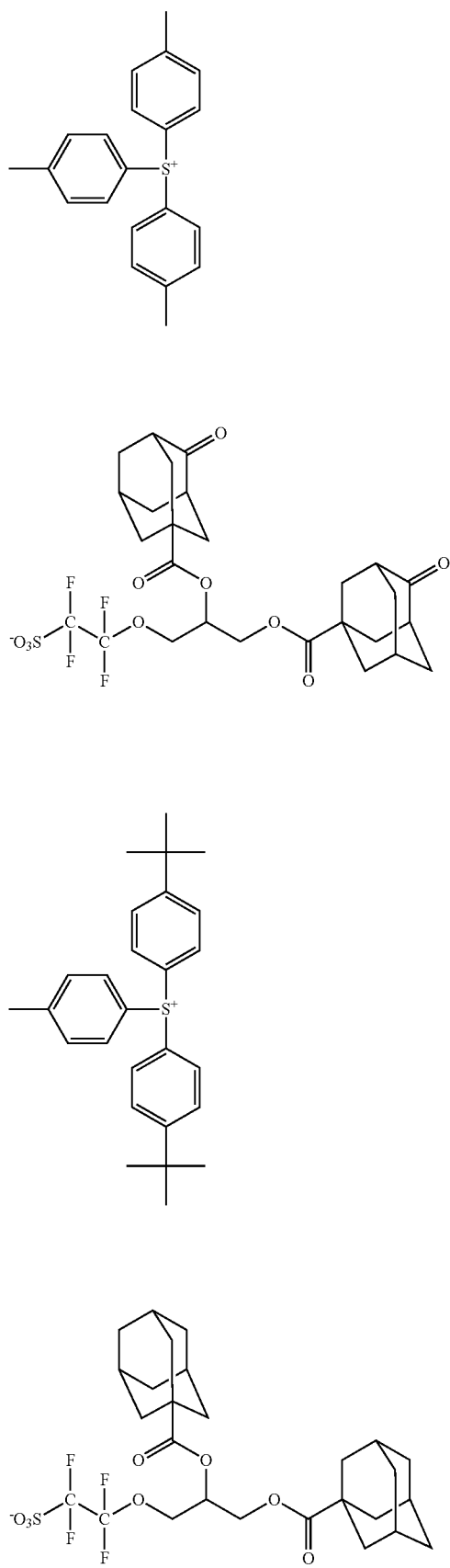

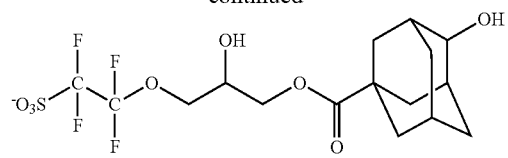
(I-23)
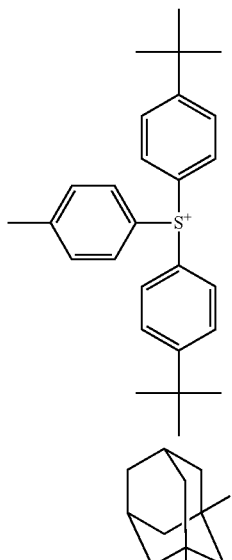
(I-24)
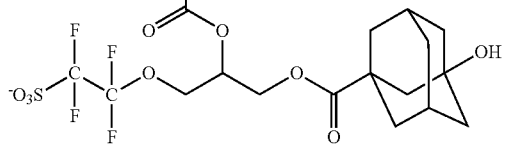
(I-25)
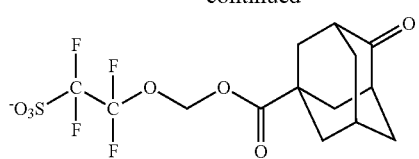
(I-26)
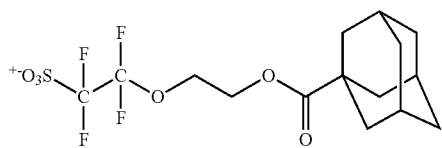
(I-27)
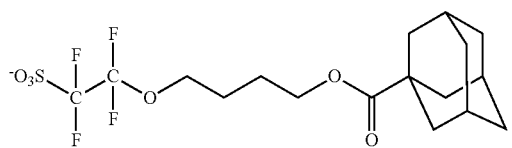
(I-28)
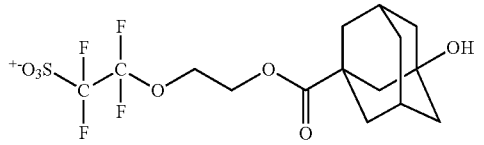

(I-29)
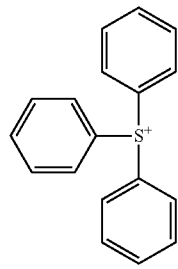
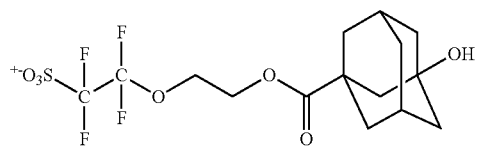
(I-30)
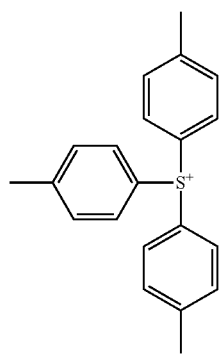
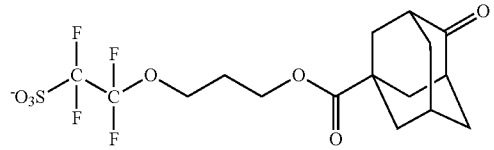
(I-31)
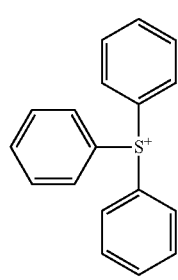
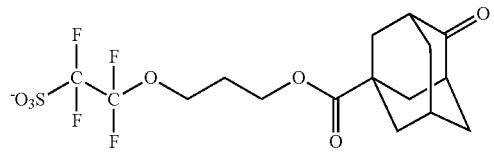
(I-32)
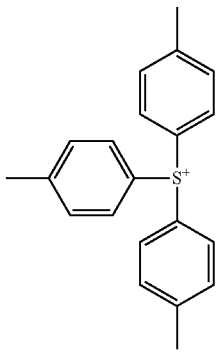
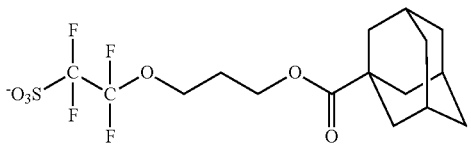
(I-33)
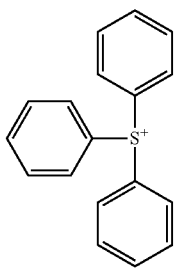
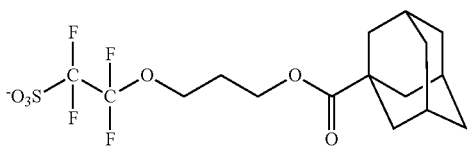
(I-34)
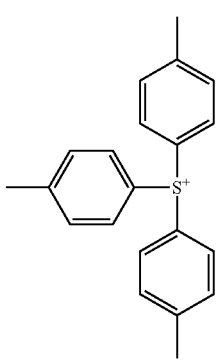
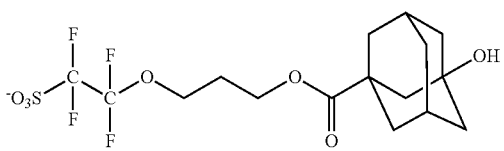

(I-35)
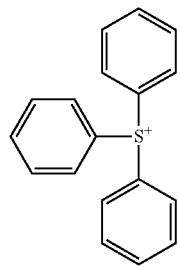
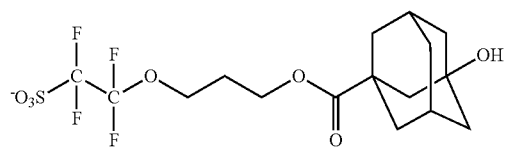
(I-36)
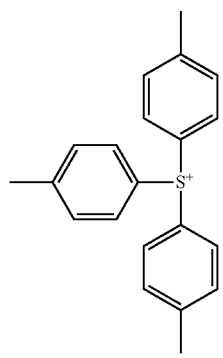
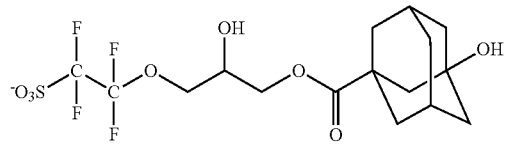
(I-37)
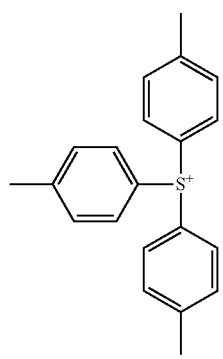
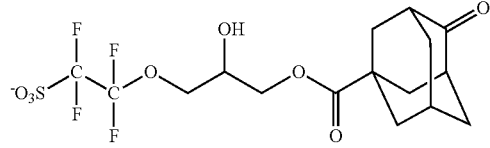
(I-38)
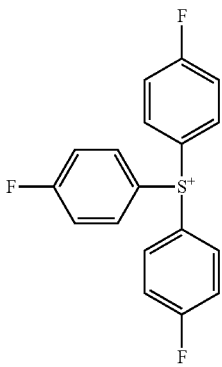
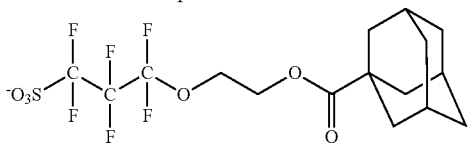
(I-39)
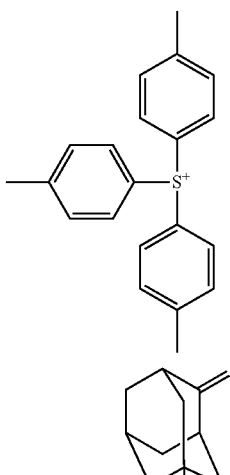
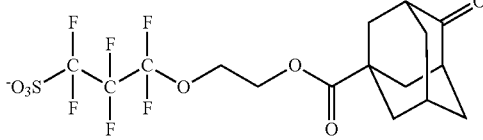
(I-40)
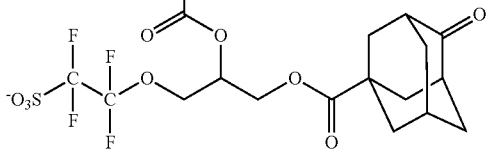

(I-41)
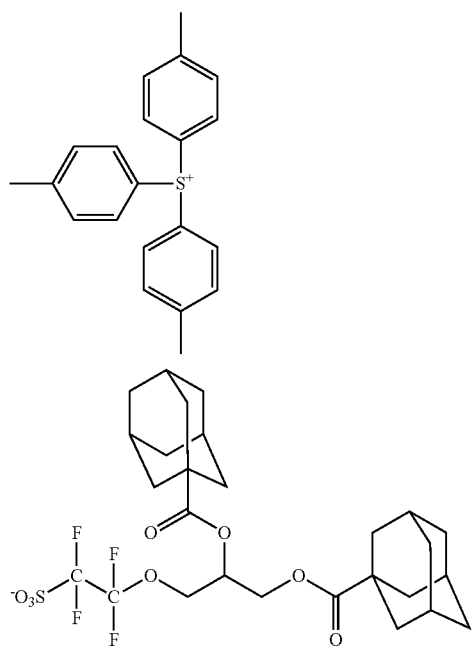
(I-42)
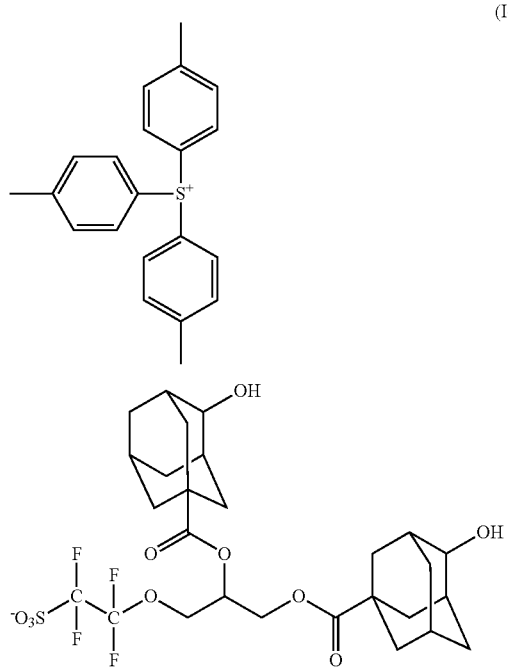
(I-43)
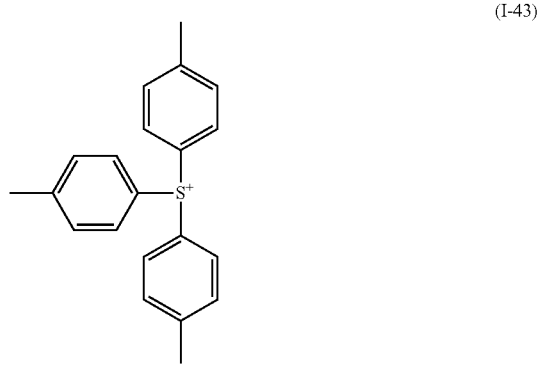
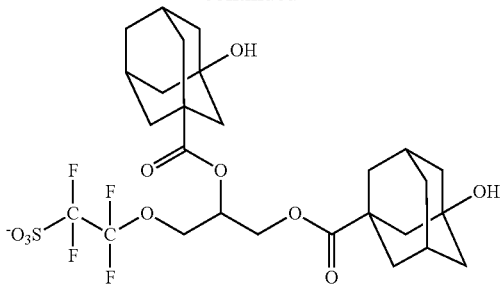
(I-44)
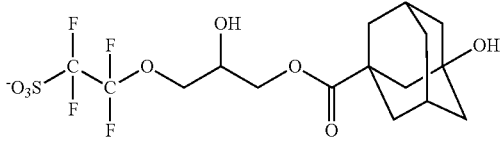
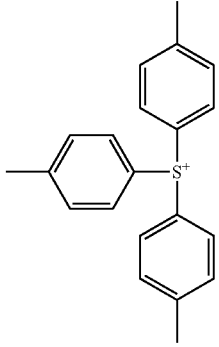
(I-45)
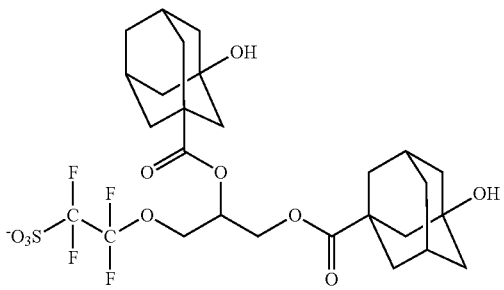

(I-46)
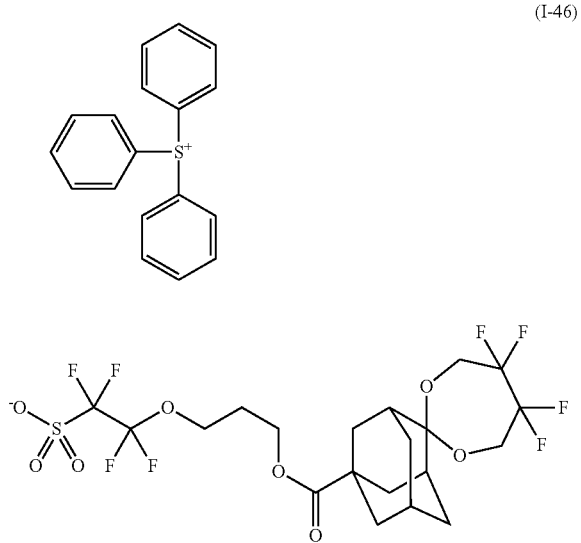
(I-47)
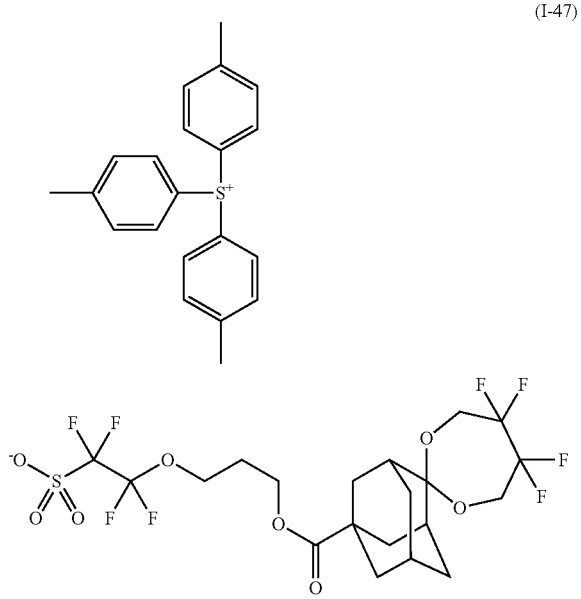
(I-48)
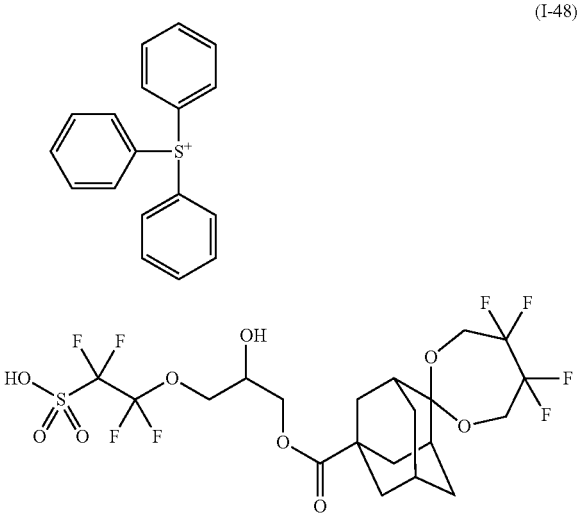
(I-49)
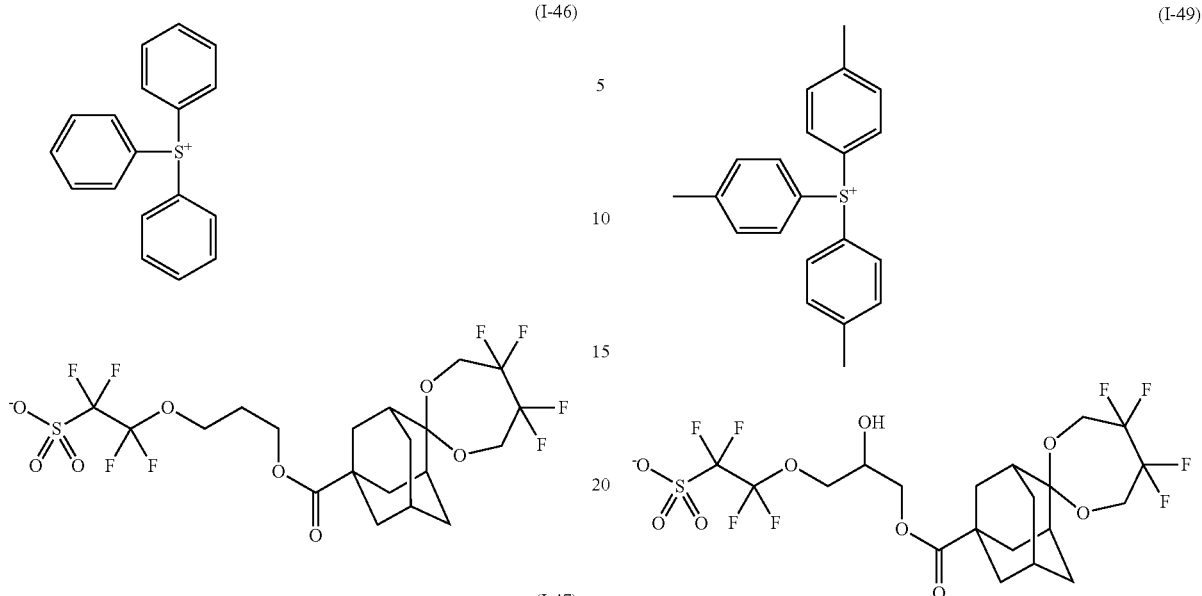
(I-50)
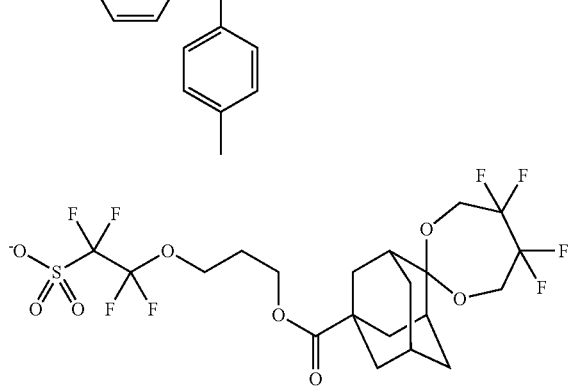
(I-51)
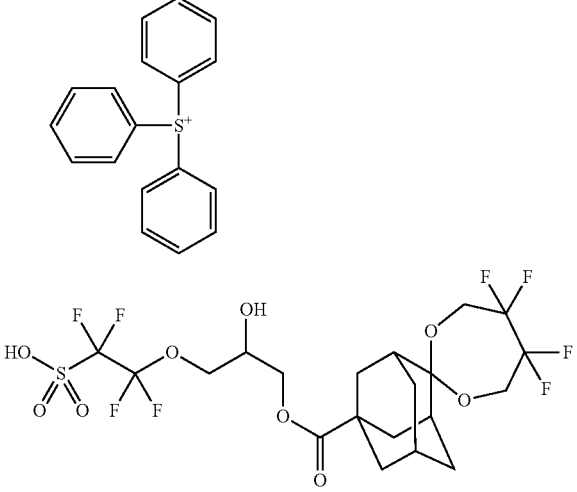

-continued

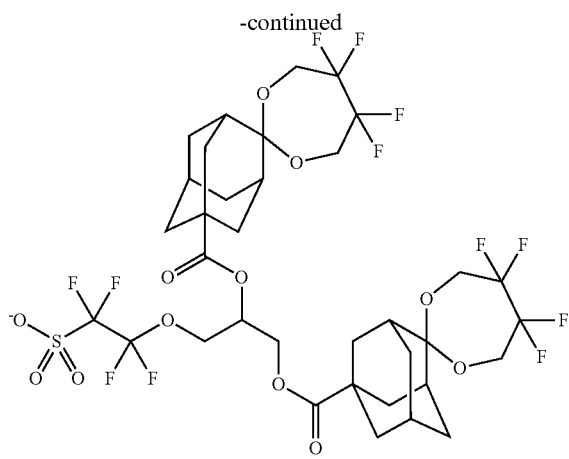

More preferred examples of SALT (I) include those represented by formulae (I-7), (I-9), (I-11), (I-12), (I-15), (I-18), (I-21), (I-22), (I-30), (I-31), (I-32), (I-33), (I-34) and (I-51).

The process for producing SALT (I) will be illustrated. The SALT (I) can be produced by condensing an alcoholic hydroxy group-containing compound with a carboxy group-containing compound, as necessary in the presence of a silver oxide or silver perchlorate, in an organic solvent such as chloroform, dichloromethane, dichloroethane, methanol, dimethylformamide or acetonitrile, shown as bellow.

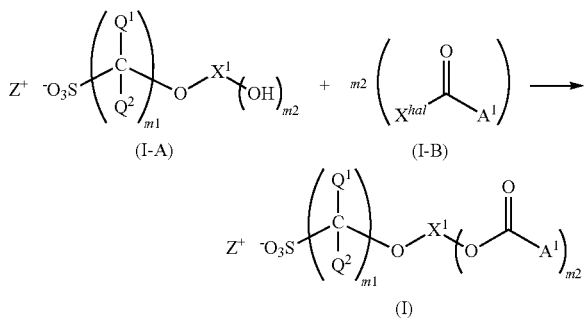

wherein $Q^1, Q^2, A^1, X^1, Z^+$, m1 and m2 are defined as above, $X^{hal}$ is a leaving group, typically a halogen atom such as fluorine atom, chlorine atom or iodine atom.

Examples of the alcoholic hydroxy group-containing compound include the compound represented by formula (I-A-a) and the compound represented by formula (I-A-e).

When the compound represented by formula (I-A) is represented by formula (I-A-e):

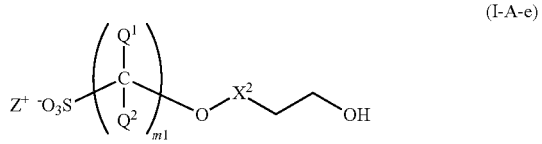

wherein $Q^1, Q^2, X^2, Z^+$ and m1 are defined as above, i.e., one of the salts represented by formula (I-A), the compound can be produced by conducting hydroboration of a compound represented by formula (I-A-f), followed by oxidizing the obtained compound:

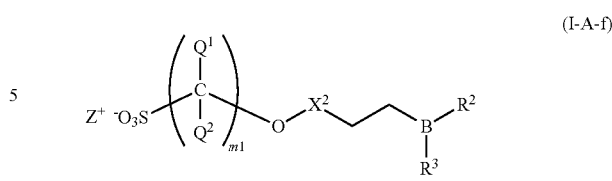

wherein $R^2$ and $R^3$ independently represent C1 to C10 saturated hydrocarbon group, or $R^2$ and $R^3$ are bonded together with B to form a ring, $X^2$ is a C1-C8 saturated aliphatic hydrocarbon group, and $Q^1, Q^2, Z^+$ and m1 are defined as above.

The hydroboration can be conducted using a borane compound such as diethylborane, catechol borane or 9-borabicyclo[3.3.1]nonane [9-BBN], together with hydrogen peroxide or m-chloroperoxybenzoic acid [m-CPBA], in an aqueous alkaline solution such as an aqueous sodium hydroxide.

When the compound represented by formula (I-A) is represented by

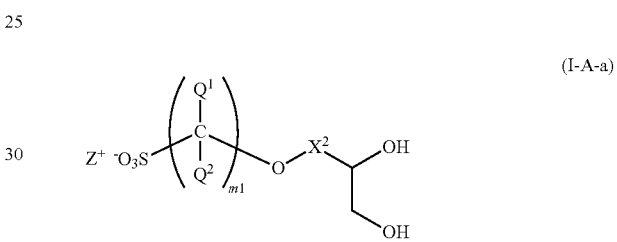

formula (I-A-a):
wherein $Q^1, Q^2, Z^+$ and m1 are defined as above, $X^2$ is a C1-C8 saturated aliphatic hydrocarbon group.

The compound represented by formula (I-A-a) may be produced by oxidizing the compound represented by formula (I-A-b)

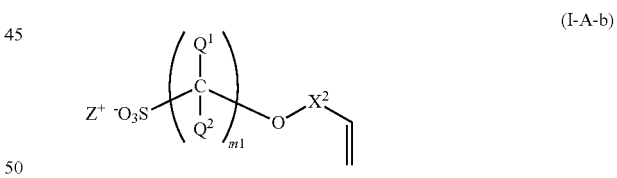

wherein $Q^1, Q^2, Z^+, X^2$ and m1 are defined as above, using an oxidizing agent in the presence of silver oxide or silver peroxide in an organic solvent.

The oxidizing agent usually contains a metal compound selected from the group consisting of osmium, palladium, rhodium, ruthenium, tungsten, manganese, iron and copper. The oxidizing agent may contain the metal compound in its catalytic amount together with periodic acid salt or N-methyl-morpholine-O-oxide.

The organic solvent includes chloroform, dichloromethane, dichloroethane, methanol, dimethylformamide and acetonitrile. The compound represented by formula (I-A-b) can be produced by mixing the compound represented by formula (I-A-d)

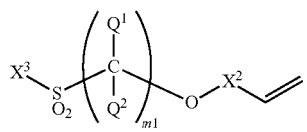
(I-A-d)

wherein $Q^1$, $Q^2$, $X^2$ and m1 are defined as above, and $X^3$ represents fluorine, chlorine or bromine, $$Z^+X^-$$ (I-A-c)

with the compound represented by formula (I-A-c)
wherein $Z^+$ are defined as above, and $X^-$ represents fluorine, chlorine, bromine, methylsulfonate, methylmethane sulfate, chloric acid or perchloric acid,
under a basic condition formed by using triethylamine, pyridine, piperidine, N-methylmorpholine, sodium hydroxide, potassium hydroxide, potassium carbonate, sodium carbonate, potassium hydrogencarbonate or sodium hydrogencarbonate.

The compound represented by formula (I-A-d) includes 2-allyloxy-1,1,2,2-tetrafluoroethane sulfonyl fluoride which is available on the market. The compound represented by formula (I-A-d) can be produced by reacting a corresponding olefin compound with a sulton described in Journal of fluorine chemistry, 1990, vol. 46, p. 21-38.

Examples of the carboxy group-containing compound include amadantane carbonyl chloride and cyclohexane carbonyl chloride, i.e., the compound represented by formula (I-B). The compound represented by formula (I-B) is available on the market.

A variety of the photoresist compositions can be obtained by modify the group $A^1$ of the salt of the formula (I) in a manner known to the field of the invention, such as acetalization, esterification, oxidation, or reduction.

Hereinafter, the photoresist composition of the present invention will be illustrated.

The photoresist composition comprises SALT (I) and a resin which is hardly soluble or insoluble but soluble in an aqueous alkali solution by action of an acid.

The photoresist composition of the present invention comprises SALT (I) so that it can provide a photoresist pattern substantially free from Line width Roughness.

The SALT (I) works as an acid generator in the photoresist composition. The photoresist composition of the present invention may comprise other acid generators than the SALT (I). The photoresist composition may comprise, if necessary, a basic compound which is a quencher known in the art, and a solvent.

The other acid generators than the SALT (I) include known acid generators. The other acid generators than SALT (I) may be either ionic or non-ionic one.

The other acid generators than SALT (I) may be a salt comprising different cation and anion from those of SALT (I), or a salt comprising the same cation as SALT (I) and a different known anion from that of SALT (I).

The other acid generators than the SALT (I) include those represented by formula (B1-1), formula (B1-2), formula (B1-3), formula (B1-4), formula (B1-5), formula (B1-6), formula (B1-7), formula (B1-8), formula (B1-9), formula (B1-10), formula (B1-11), formula (B1-12), formula (B1-13), formula (B1-14), formula (B1-15), formula (B1-16), formula (B1-17), formula (B1-18), formula (B1-19) and formula (B1-20). Among them, preferred are compounds having triphenylsulfonium cation and compounds having tritolylsulfonium cation, and more preferred are compounds represented by formula (B1-1), formula (B1-2), formula (B1-3), formula (B1-6), formula (B1-11), formula (B1-12), formula (B1-13) and formula (B1-14).

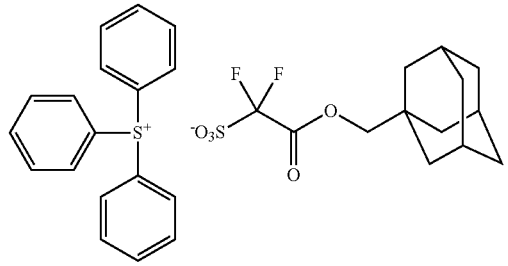
(B1-1)

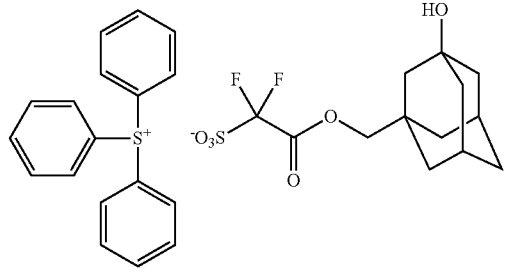
(B1-2)

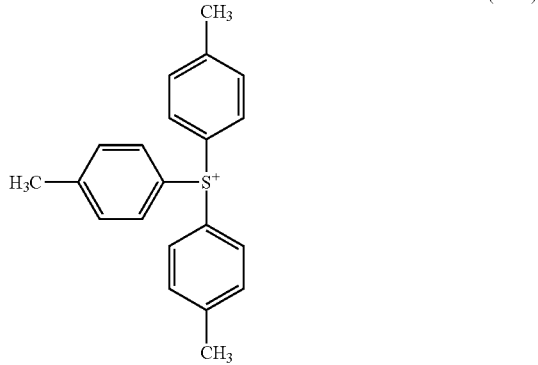
(B1-3)

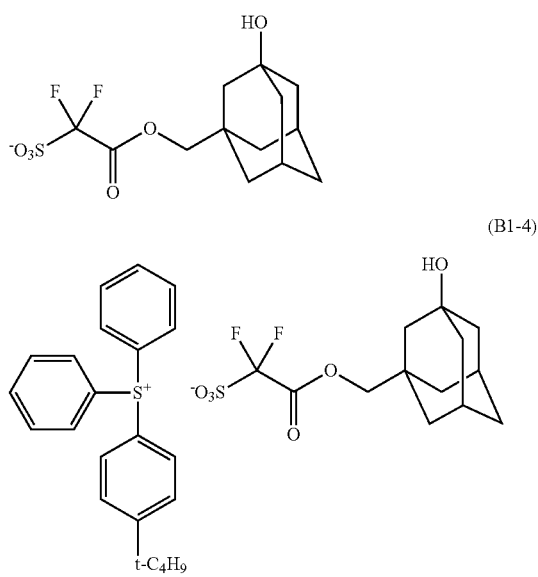
(B1-4)

(B1-5)
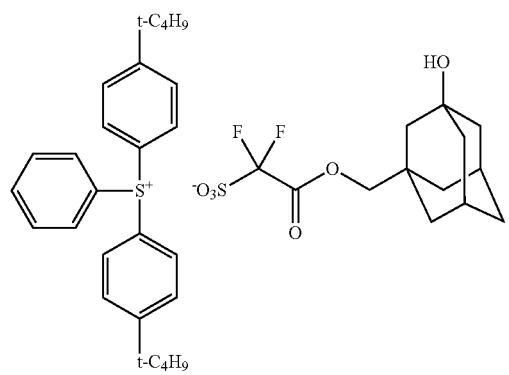
(B1-6)
(B1-7)
(B1-8)
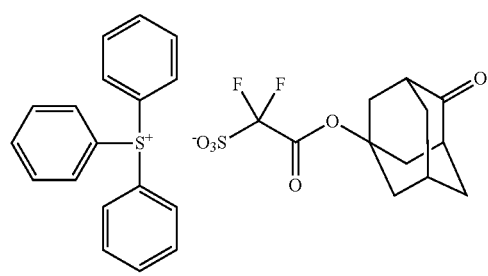
(B1-9)
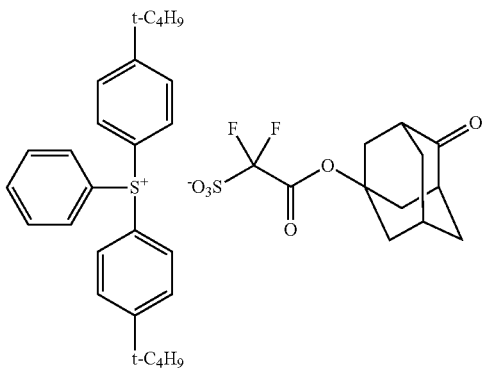
(B1-10)
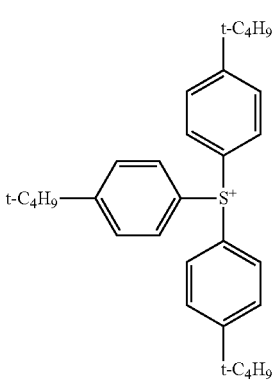
(B1-11)
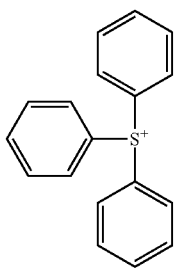
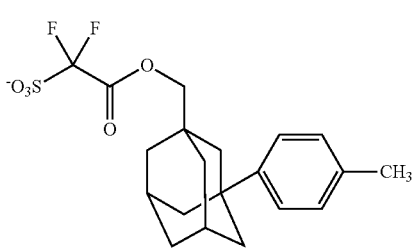

-continued (B1-12)
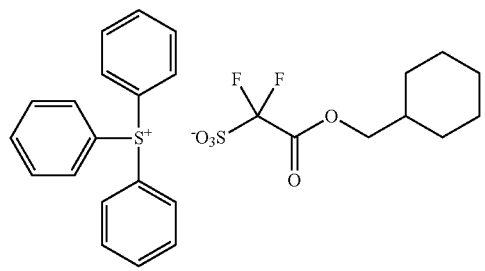

(B1-13)
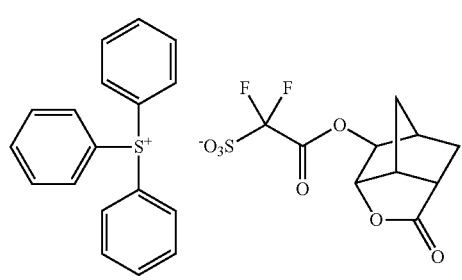

(B1-14)
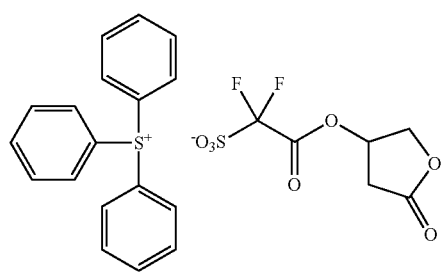

(B1-15)
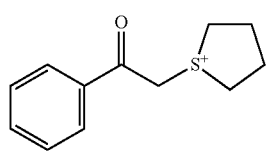

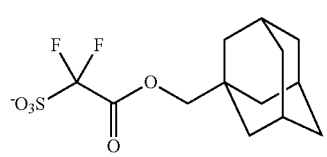

(B1-16)
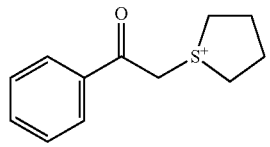

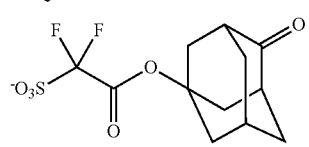

-continued (B1-17)
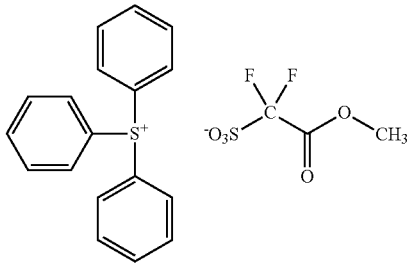

(B1-18)
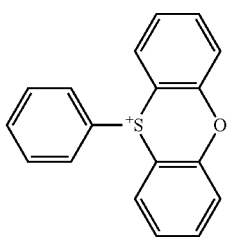

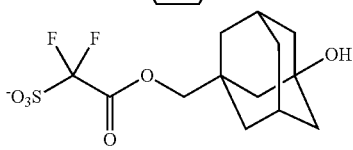

(B1-19)
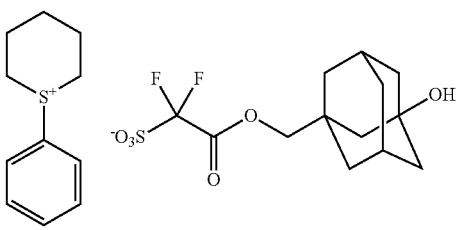

(B1-20)
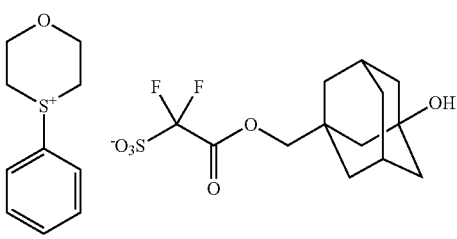

The resin for the photoresist composition of the present invention is hardly soluble or insoluble but soluble in an aqueous alkali solution by action of an acid. With such resin as having the above-mentioned properties, the photoresist composition can give a photoresist pattern by an acid generated from the acid generator as mentioned above.

Herein, "soluble in an aqueous alkali solution by the action of an acid" means such property as soluble in an aqueous alkali solution by contacting it with into an acid while hardly soluble or insoluble in an aqueous alkali solution before contacting it with into an acid.

The resin for the photoresist composition of the present invention has an acid-labile group. Such resin can be produced by polymerizing one or more kinds of monomers having an acid-labile group.

Herein "an acid-labile group" refers to a group capable of being cleaved in case of contacting with an acid to give a hydrophilic group such as a hydroxy group or carboxy group.

Specific examples of the acid-labile group include a group represented by the formula (1):

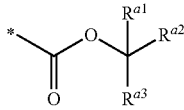
(1)

wherein $R^{a1}$, $R^{a2}$ and $R^{a3}$ independently each represent a C1-C8 alkyl group or a C3-C20 alicyclic hydrocarbon group, and $R^{a1}$ and $R^{a2}$ may be bonded each other to form a C2-C20 divalent hydrocarbon group,
and * represents a binding position,
and a group represented by the formula (2)

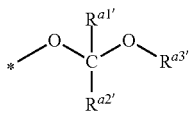
(2)

wherein $R^{a1'}$ and $R^{a2'}$ independently each represent a hydrogen atom or a C1-C12 monovalent hydrocarbon group, and $R^{a3'}$ represents a C1-C20 monovalent hydrocarbon group, or $R^{a3'}$ binds to $R^{a2'}$ together with —CO— attaching to $R^{a2'}$ and $R^{a3'}$ to form C3-C20 ring in which a methylene group of the divalent hydrocarbon group may be replaced by —O— or —S—.

Specific examples of the C1-C8 alkyl group include a methyl group, an ethyl group, a propyl group, an isopropyl group, a butyl group, a pentyl group, a hexyl group, a heptyl group and an octyl group.

The alicyclic hydrocarbon group may be monocyclic or polycyclic. Examples of the alicyclic hydrocarbon group include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the followings.

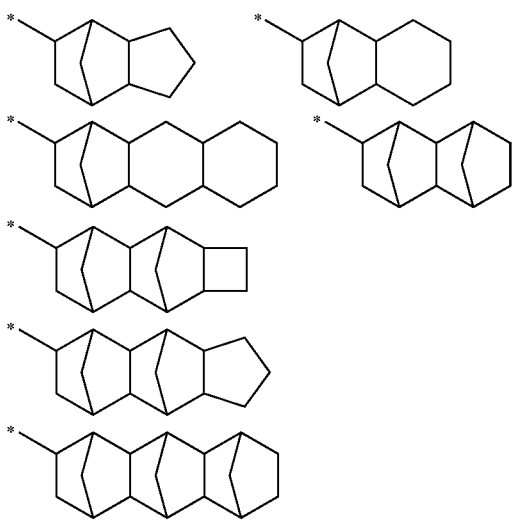

The alicyclic hydrocarbon group preferably has 5 to 16 carbon atoms.

When $R^{a1}$ and $R^{a2}$ of formula (1) are bonded each other to form a C2-C20 divalent hydrocarbon group, the moiety represented by —C($R^{a1}$)($R^{a2}$)($R^{a3}$) includes the following groups and the ring preferably has 3 to 12 carbon atoms:

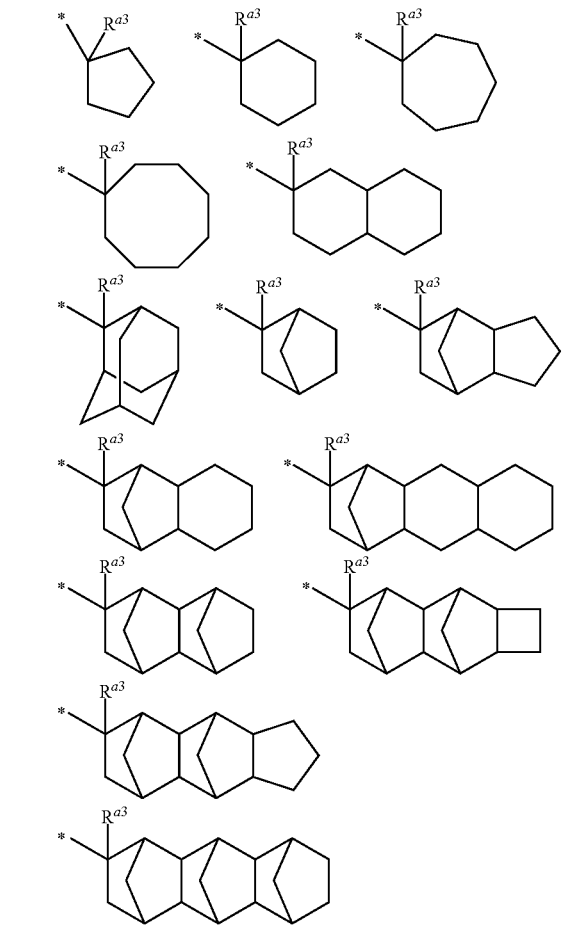

wherein $R^{a3}$ is the same as defined above and * represents a binding position to —O— of formula (1).

The group represented by the formula (1) wherein $R^{a1}$, $R^{a2}$ and $R^{a3}$ independently each represent a C1-C8 alkyl group such as a tert-butyl group, such as 1,1'-dialkylalkoxylcarbonyl group, the group represented by the formula (1) wherein $R^{a1}$ and $R^{a2}$ are bonded each other to form an adamantyl ring and $R^{a3}$ is a C1-C8 alkyl group such as a 2-alkyladaman-2-tyloxycarbonyl group, and the group represented by the formula (1) wherein $R^{a1}$ and $R^{a2}$ are C1-C8 alkyl groups and $R^{a3}$ is an adamantin-1-yl group such as a 1-(1-adaman-1-yl)-1-alkylalkoxycarbonyl group are preferable.

As to formula (2), examples of the hydrocarbon group include an alkyl group, an alicyclic hydrocarbon group and an aromatic hydrocarbon group.

Examples of the alkyl group and the alicyclic hydrocarbon group include the same as described above. Examples of the aromatic hydrocarbon group include an aryl group such as a phenyl group, a naphthyl group, a p-methylphenyl group, a p-tert-butylphenyl group, a p-adamantylphenyl group, a tolyl group, a xylyl group, a cumyl group, a mesityl group, a biphenyl group, an anthryl group, a phenanthryl group, a 2,6-diethylphenyl group and a 2-methyl-6-ethylphenyl group.

It is preferred that at least one of $R^{a1'}$ and $R^{a2'}$ is a hydrogen atom.

Examples of the group represented by formula (2) include the following.

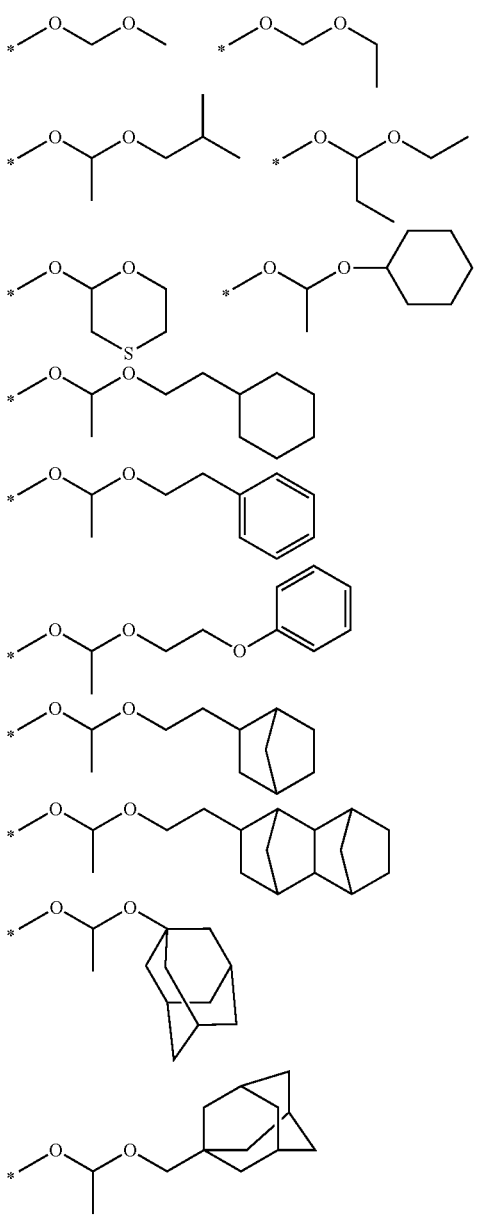

The monomer having an acid-labile group, preferably one represented by formula (1) and/or formula (2) is preferably a monomer having an acid-labile group and carbon-carbon double bond, more preferably a (meth)acryalte compound having an acid-labile group.

Such (meth)acryalte compound preferably has a C5-C20 alicyclic hydrocarbon group. Since the resin produced from (meth)acryalte compound having C5-C20 alicyclic hydrocarbon group has a bulky structure, the photoresist composition comprising the resin can show more excellent resolution.

Hereinafter, the resin produced from (meth)acryalte compound having C5-C20 alicyclic hydrocarbon group is sometimes referred to as "resin (A)".

Preferable resin (A) has a structural unit represented by the formula (a1-1) or (a1-2):

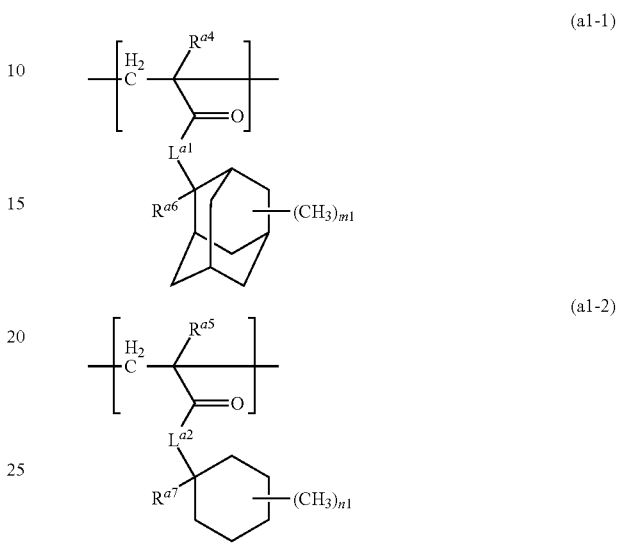

wherein $R^{a4}$ and $R^{a5}$ each independently represents a hydrogen atom or a methyl group, $R^{a6}$ and $R^{a7}$ each independently represents a C1-C10 aliphatic hydrocarbon group, $L^{a1}$ and $L^{a2}$ each independently represents *—O— or *—O—$(CH_2)_{k1}$—CO—O— in which * represents a binding position to —CO—, and k1 represents an integer of 1 to 7, and m1 represents an integer of 0 to 14, n1 represents an integer of 0 to 10.

Examples of the aliphatic hydrocarbon group include a C1-C10 alkyl group such as a methyl group, an ethyl group, a propyl group, an isopropyl group, a butyl group, a tert-butyl group, 2,2-dimethylethyl group, 1-methylpropyl group, 2,2-dimethylpropyl group, 1-ethylpropyl group, 1-methylbutyl group, 2-methylbutyl group, 3-methylbutyl group, 1-propylbutyl group, a pentyl group, 1-methylpentyl group, a hexyl group, 1,4-dimethylhexyl group, a heptyl group, 1-methylheptyl group and an octyl group; and the saturated cyclic hydrocarbon group such as a cyclohexyl group, a methylcyclohexyl group, a dimethylcyclohexyl group, a cycloheptyl group, a methylcycloheptyl group, a norbornyl group and a methylnorbornyl group.

The alkyl group has preferably 1 to 8 carbon atoms, more preferably 1 to 6 carbon atoms, and the saturated cyclic hydrocarbon group preferably has 3 to 10 carbon atoms and more preferably 3 to 6 carbon atoms.

$L^{a1}$ and $L^{a2}$ are preferably *—O— or *—O—$(CH_2)_{f1}$—CO—O— in which * represents a binding position to —CO—, and f1 represents an integer of 1 to 4, and is more preferably *—O— or *—O—$CH_2$—CO—O—, and is especially preferably *—O—.

In the formula (a1-1), m1 is preferably an integer of 0 to 3, and is more preferably 0 or 1. In the formula (a1-2), n1 is preferably an integer of 0 to 3, and is more preferably 0 or 1.

$R^{a4}$ and $R^{a5}$ are preferably methyl groups.

The compound from which the structural unit represented by (a1-1) is derived includes the compounds mentioned in JP2010-204646.

As the structural unit represented by the formula (a1-1), preferred are structural units represented by formulae (a1-1-1), (a1-1-2), (a1-1-3), (a1-1-4), (a1-1-5), (a1-1-6), (a1-1-7) and (a1-1-8), more preferred are structural units represented by formulae (a1-1-1), (a1-1-2) and (a1-1-3).

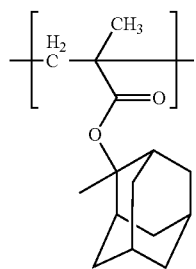
(a1-1-1)

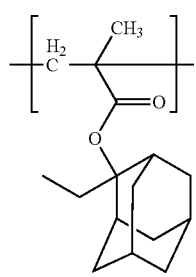
(a1-1-2)

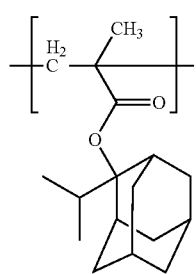
(a1-1-3)

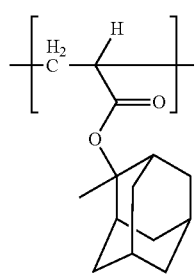
(a1-1-4)

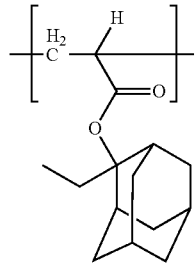
(a1-1-5)

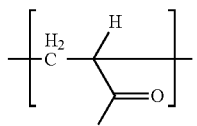
(a1-1-6)

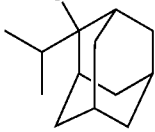
(a1-1-7)

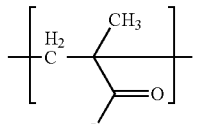

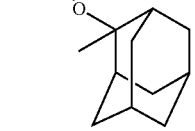
(a1-1-8)

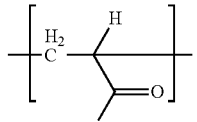

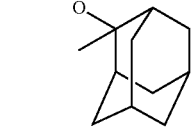

Examples of structural units represented by the formula (a1-2) include 1-ethyl-cyclopentant-1-yl(meth)acrylate, 1-ethyl-cyclohexan-1-yl(meth)acrylate, 1-ethyl-cyclohept-1-yl (meth)acrylate, 1-methyl-cyclopent-1-yl(meth)acrylate, and 1-isopropyl-cyclopent-1-yl(meth)acrylate.

As the structural unit represented by the formula (a1-2), preferred are those represented by formulae (a1-2-1), (a1-2-2), (a1-2-3), (a1-2-4), (a1-2-5) and (a1-2-6), more preferred are those represented by formulae (a1-2-3) and (a1-2-4), and still more preferred are those represented by formula (a1-2-3).

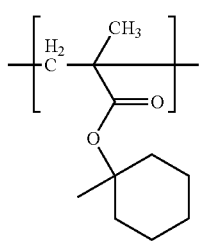
(a1-2-1)

-continued (a1-2-2)
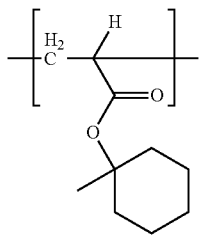

(a1-2-3)
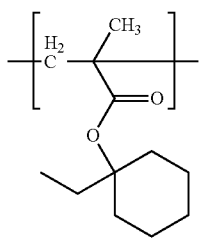

(a1-2-4)
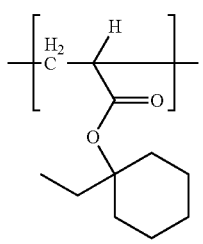

(a1-2-5)
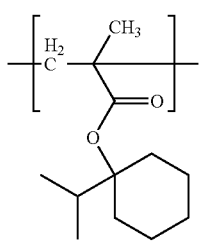

(a1-2-6)
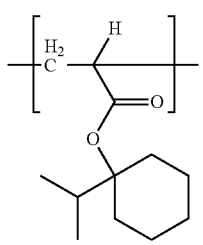

The content of the structural unit represented by the formula (a1-1) and/or the formula (a1-2) in the resin (A) is usually 10 to 95% by mole, preferably 15 to 90% by mole, and more preferably 20 to 85% by mole based on 100% by mole of all the structural units of the resin (A).

When the resin (A) has an adamantane ring-containing structural unit, preferably the structural unit represented by formula (a1-1), the content of the adamantane ring-containing structural unit is preferably 15% by mole or more, and more preferably 20% by mole or more based on 100% by mole of all the structural unit represented by formula (a1). When the resin (A) has an adamantane ring-containing structural unit in such amount as mentioned above, the photoresist pattern obtained from the photoresist composition comprising the resin (A) can have more improved resistance to dry-etching. The content of the structural unit represented by the formula (a1-1) and/or the formula (a1-2) can be controlled by adjusting the amount of the compounds from which the structural unit represented by the formula (a1-1) and/or the formula (a1-2) is derived at production of the resin (A).

The resin (A) may further comprise a structural unit having no acid-labile group. The resin (A) may further comprise one or more kinds of structural units having no acid-labile group. The content of the structural unit having an acid-labile group is preferably 10 to 80% by mole, more preferably 20 to 60% by mole of the total mole amount of all of structural units in the resin (A).

In case where the resin (A) comprise a structural unit having no acid-labile group, the molar ratio of the structural unit having an acid-labile group to the structural unit having no acid-labile group is preferably (10-80)/(90-20), more preferably (20-60)/(80-40) [=(the structural unit having an acid-labile group/the structural unit having no acid-labile group)].

When the resin (A) has the structural units in such amount as mentioned above, the photoresist pattern obtained from the photoresist composition comprising the resin (A) can have more improved resistance to dry-etching.

The structural unit having no acid-labile group preferably has a hydroxy group or a lactone ring.

When the resin (A) has a structural unit having no acid-labile group but having a hydroxy group or a lactone ring, the photoresist composition comprising such resin can show adhesiveness of photoresist to a substrate and provide a photoresist pattern with good resolution.

The resin (A) may comprise one or more kinds of structural units having no acid-labile group but having a hydroxy group.

The structural unit having no acid-labile group in the resin (A) can be suitably selected depending on exposure source for producing photoresist pattern from the photoresist composition having comprising the resin (A).

When KrF excimer laser (wavelength: 248 nm) lithography system, or a high energy laser such as electron beam and extreme ultraviolet is used as an exposure system, preferred is a resin which has the structural unit having no acid-labile group but having a phenolic-hydroxy group. When ArF excimer laser (wavelength: 193 nm) is used as an exposure system, preferred is a resin which has the structural unit represented by the formula (a2-1).

The structural unit having no acid-labile group but having a hydroxy group preferably has a hydroxyadamantyl group.

Preferred examples of the structural unit having no acid-labile group but having a hydroxy group include a structural unit represented by the formula (a2-1):

(a2-1)
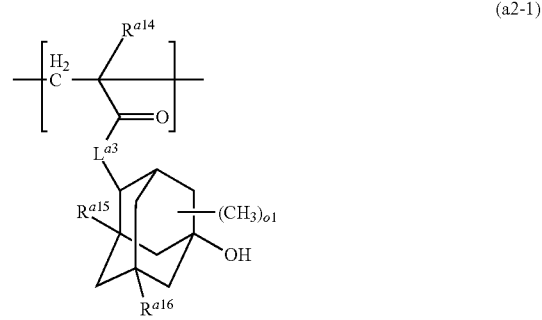

wherein $R^{a14}$ represents a hydrogen atom or a methyl group, $R^{a15}$ and $R^{a16}$ each independently represent a hydrogen atom, a methyl group or a hydroxy group, $L^{a3}$ represents *—O— or *—O—$(CH_2)_{k2}$—CO—O— in which * represents a binding position to —CO—, and k2 represents an integer of 1 to 7, and o1 represents an integer of 0 to 10.

In the formula (a2-1), $R^{a14}$ is preferably a methyl group, $R^{a15}$ is preferably a hydrogen atom, $R^{a16}$ is preferably a hydrogen atom or a hydroxy group, $L^{a3}$ is preferably *—O— or *—O—$(CH_2)_{f2}$—CO—O— in which * represents a binding position to —CO—, and f2 represents an integer of 1 to 4, is more preferably *—O— and *—O—$CH_2$—CO—O—, and is still more preferably *—O—, and o1 is preferably 0, 1, 2 or 3 and is more preferably 0 or 1.

The structural unit represented by the formula (a2-1) includes those represented by the formula as follow:

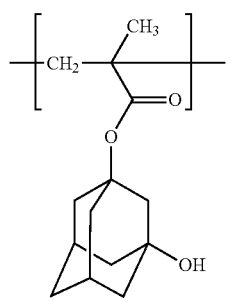

(a2-1-1)

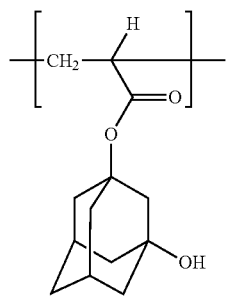

(a2-1-2)

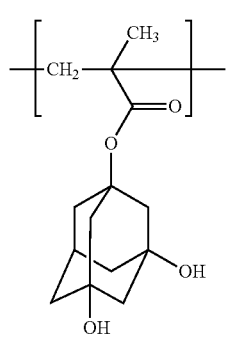

(a2-1-3)

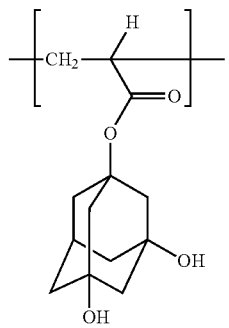

(a2-1-4)

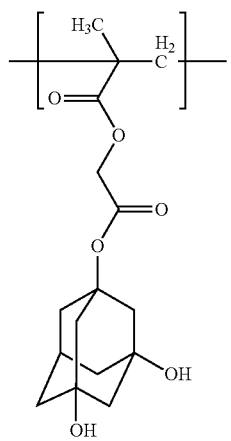

(a2-1-5)

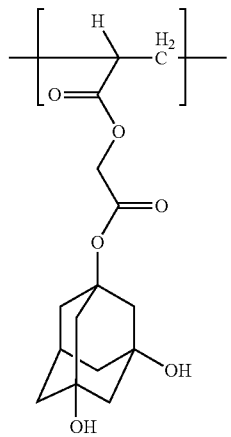

(a2-1-6)

The structural unit represented by formula (a2-1) includes those derived from the compounds mentioned in JP2010-204646A.

Among them, preferred are the structural units represented by formulae (a2-1-1), (a2-1-2), (a2-1-3) and (a2-1-4), more preferred are the structural units represented by formulae (a2-1-1) and (a2-1-3).

When the resin has the structural unit represented by the formula (a2-1), the content of the structural unit represented by the formula (a2-1) is usually 3 to 40% by mole, and preferably 5 to 35% by mole, and more preferably 5 to 30% by mole, based on total molar of all the structural units of the resin.

Examples of the structural unit having no acid-labile group and having a hydroxy group include one represented by the formula (a2-0):

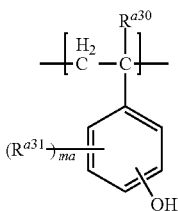

(a2-0)

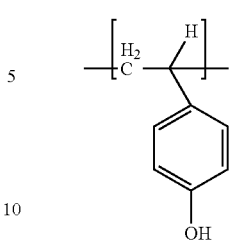

(a2-0-2)

wherein $R^{a30}$ represents a hydrogen atom, a halogen atom, a C1-C6 alkyl group or a C1-C6 halogenated alkyl group, $R^{a31}$ is independently in each occurrence a halogen atom, a hydroxy group, a C1-C6 alkyl group, a C1-C6 alkoxy group, a C2-C4 acyl group, a C2-C4 acyloxy group, an acryloyl group or a methacryloyl group, ma represents an integer of 0 to 4.

In the formula (a2-0), examples of the halogen atom include a fluorine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group. Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. $R^{a30}$ represents preferably a C1-C4 alkyl group, more preferably a C1-C2 alkyl group, and still more preferably a methyl group.

Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group. Examples of the C2-C4 acyl group include an acetyl group, a propionyl group and a butyryl group, and examples of the C2-C4 acyloxy group include an acetyloxy group, a propionyloxy group and a butyryloxy group. $R^{a31}$ represents preferably a C1-C4 alkoxy group, more preferably a C1-C2 alkoxy group, and still more preferably a methoxy group.

In the formula (a2-0), ma is preferably 0, 1 or 2, and is more preferably 0 or 1, and especially preferably 0.

The structural unit represented by the formula (a2-0) is preferably represented by the formulae (a2-0-1) and (a2-0-2). Monomers from which such unit is derived include compounds mentioned in JP2010-204634A.

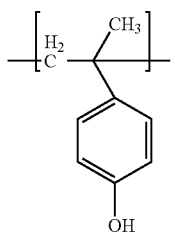

(a2-0-1)

The resin having the structural unit represented by the formula (a2-0) can be produced, for example, by polymerizing a compound in which a hydroxy group has been protected with a protecting group such as an acetyl group and from which the structural unit represented by the formula (a2-0) is derived, followed by conducting deprotection of the obtained polymer with an acid or a base.

The resin having the structural unit represented by the formula (a2-0) can be produced from a hydroxylstylene as a monomer. Among them, preferred are 4-hydroxystyrene and 4-hydroxy-α-methylstyrene.

When such resin is produced from a hydroxylstylene, it can be produced by protecting a phenolic hydroxy group with an acetyl group to produce acetylhydroxylstylene, polymerizing acetylhydroxylstylene to obtain a resin having the structural unit represented by the formula (a2), followed by deprotecting acetylhydroxy groups of the resin to obtain a resin having the structural unit represented by the formula (a2-0). The deprotection of acetylhydroxy groups requires not remarkably detracting from other structural units such as the unit (a1).

When the resin (A) has the structural unit represented by the formula (a2-0), the content of the structural unit represented by the formula (a2-0) is usually 10 to 90% by mole and preferably 10 to 85% by mole and more preferably 15 to 80% by mole based on total molar of all the structural units of the resin.

As to the structural unit having no acid-labile group but having a lactone ring, examples of the lactone ring include a monocyclic lactone ring such as β-propiolactone ring, γ-butyrolactone ring and δ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of the structural unit having no acid-labile group but having a lactone ring include those represented by the formulae (a3-1), (a3-2) and (a3-3):

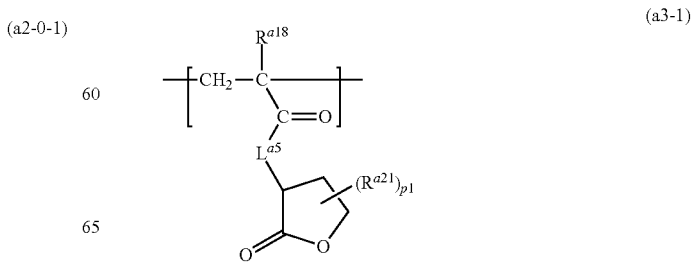

(a3-1)

(a3-2)

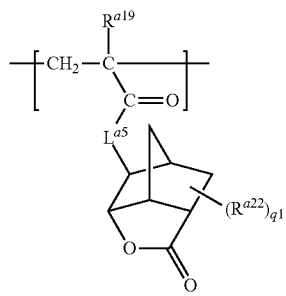

(a3-3)

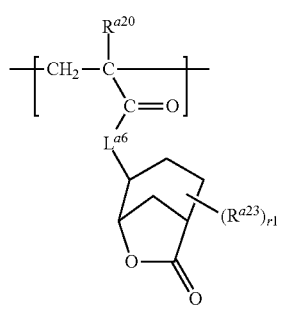

wherein $L^{a4}$, $L^{a5}$ and $L^{a6}$ each independently represent *—O— or *—O—$(CH_2)_{k3}$—CO—O— in which * represents a binding position to —CO— and k3 represents an integer of 1 to 7, $R^{a18}$, $R^{a19}$ and $R^{a20}$ each independently represent a hydrogen atom or a methyl group, $R^{a21}$ represents a C1-C4 aliphatic hydrocarbon group, $R^{a22}$ and $R^{a23}$ are independently in each occurrence a carboxyl group, a cyano group or a C1-C4 aliphatic hydrocarbon group, and p1 represents an integer of 0 to 5, q1 and r1 independently each represent an integer of 0 to 3.

It is preferred that $L^{a4}$, $L^{a5}$ and $L^{a6}$ each independently represent *—O— or *—O—$(CH_2)_{d1}$—CO—O— in which * represents a binding position to —CO— and d1 represents an integer of 1 to 4, and it is more preferred that $L^{a4}$, $L^{a5}$ and $L^{a6}$ are *—O— and *—O—$CH_2$—CO—O—, and it is still more preferred that $L^{a4}$, $L^{a5}$ and $L^{a6}$ are *—O—.

$R^{a18}$, $R^{a19}$ and $R^{a20}$ are preferably methyl groups. $R^{a21}$ is preferably a hydrogen atom. It is preferred that $R^{a22}$ and $R^{a23}$ are independently in each occurrence a carboxyl group, a cyano group or a methyl group. It is preferred that p1 is an integer of 0 to 2, and it is more preferred that p1 is 0 or 1. It is preferred that q1 and r1 independently each represent an integer of 0 to 2, and it is more preferred that q1 and r1 independently each represent 0 or 1.

Preferred examples of the structural unit represented by the formula (a3-1) include those represented by the formula (a3-1-1), the formula (a3-1-2), the formula (a3-1-3) or the formula (a3-1-4).

(a3-1-1)

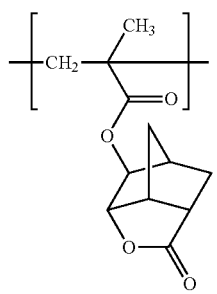

(a3-1-2)

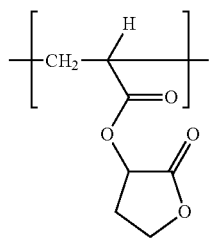

(a3-1-3)

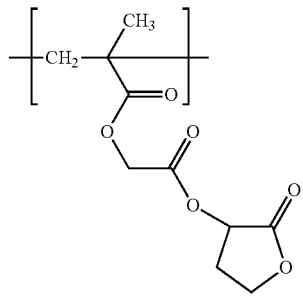

(a3-1-4)

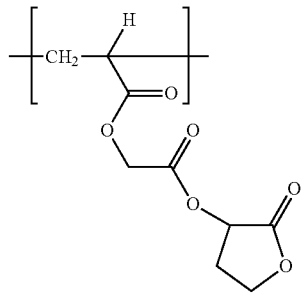

Examples of the structural unit represented by the formula (a3-2) include preferably those represented by the formula (a3-2-1), the formula (a3-2-2), the formula (a3-2-3) or the formula (a3-2-4), and more preferably those represented by the formulae (a3-2) in which $L^{a5}$ represent *—O—$CH_2$—CO—O— in which * represents a binding position to —CO— and q1=1.

(a3-2-1)

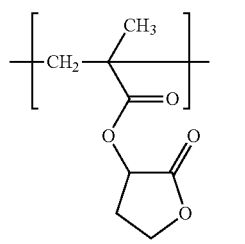

(a3-2-2)
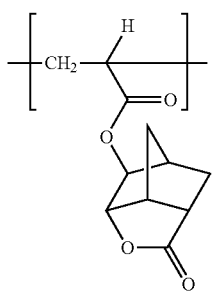

(a3-2-3)
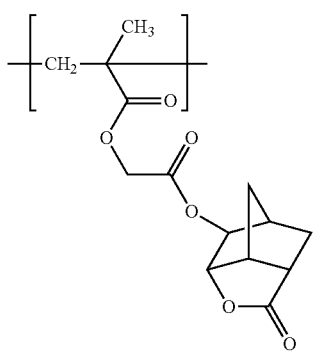

(a3-2-4)
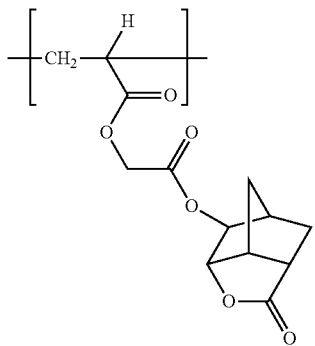

Preferred examples of the structural unit represented by the formula (a3-3) include those represented by the formula (a3-3-1), the formula (a3-3-2), the formula (a3-3-3) or the formula (a3-3-4).

(a3-3-1)
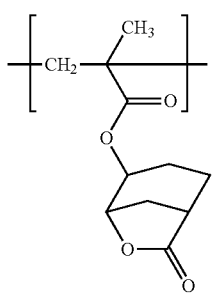

(a3-3-2)
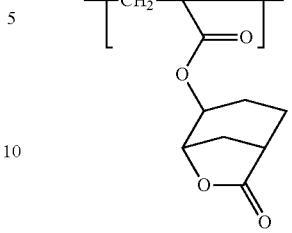

(a3-3-3)
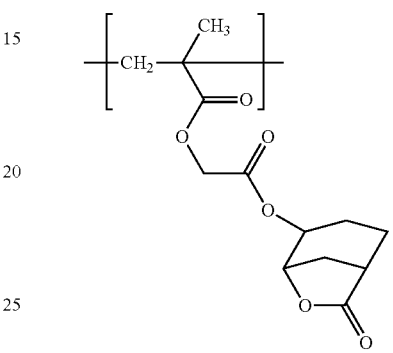

(a3-3-4)
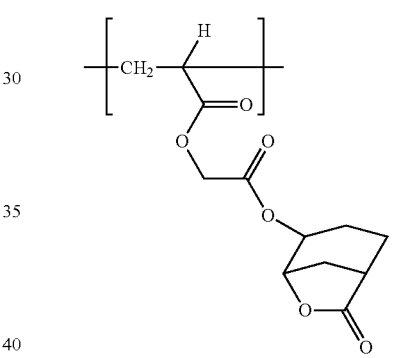

Preferred structural unit having no acid-labile group but having a lactone ring are those represented by the formulae (a3-1-3), (a3-1-4), (a3-2-1), (a3-2-2), (a3-2-3), (a3-2-4), (a3-3-3) to (a3-3-4), more preferred are those represented by the formulae (a3-2-1), (a3-2-2), (a3-2-3) and (a3-2-4), still more preferred are those represented by the formulae (a3-2-3) and (a3-2-4), especially more preferred are those represented by the formulae (a3-2-3).

Monomers from which the structural units having no acid-labile group but having a lactone ring such as those represented by the formula (a3-1), formula (a3-2) and formula (a3-3) are derived are mentioned in JP2010-204646A.

The content of the structural unit having no acid-labile group but having a lactone ring is usually 5 to 50% by mole and preferably 10 to 45% by mole based on the total molar of all structural units of the resin (A).

When the resin contains the structural unit represented by the formula (a3-1), formula (a3-2) or formula (a3-3), the content thereof is preferably 5 to 50%, more preferably 10 to 45% by mole and still more preferably 15 to 40% by mole, by mole based on total molar of all the structural units of the resin.

The structural unit having no acid-labile group may be one known in the art and other than the structural unit having no acid-labile but having a hydroxy group or a lactone ring.

The resin (A) is generally a polymer of the compound from which the structural unit having an acid labile group is derived, preferably a copolymer of the compound from which the structural unit having an acid labile group is derived and the compound from which the structural unit having no acid labile group is derived, more preferably a copolymer of the compound from which the structural unit represented by formula (a1-1) and/or formula (a1-2) is derived, and the compound from which the structural unit represented by formula (a2) and/or formula (a3) is derived.

The resin (A) preferably has a structural unit having an adamantly group such as one represented by formula (a1-1) as the structural unit having an acid-labile group.

The resin (A) preferably has a structural unit having a hydroxy adamantly group such as one represented by formula (a2-1) as the structural unit having no acid-labile group.

The resin (A) has preferably at least one selected from a structural unit having no acid-labile group but having γ-butyrolactone ring, such as one represented by formula (a3-1), and a structural unit having no acid-labile group but having a condensed lactone ring formed from γ-butyrolactone ring and a norbornane ring, such as one represented by formula (a3-2).

The resin (A) can be produced according to known polymerization methods such as radical polymerization.

The resin (A) usually has 2,500 or more of the weight-average molecular weight, preferably 3,000 or more of the weight-average molecular weight. The resin usually has 50,000 or less of the weight-average molecular weight, preferably has 30,000 or less of the weight-average molecular weight.

The weight-average molecular weight can be measured with gel permeation chromatography (standard: polyethylene).

In case of using it for producing the photoresist pattern by exposure after immersion of solution, the photoresist composition of the present invention preferably comprises, as another resin than the resin (A), a resin having the structural units represented by formula (FI):

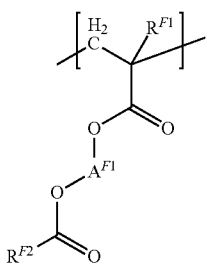

(FI)

wherein $R^{F1}$ represents a hydrogen atom or a methyl group, $A^{F1}$ represents a C1-C6 alkanediyl group, and
$R^{F2}$ represents a C1-C10 hydrocarbon group having a fluorine atom. Examples of C1-C6 alkanediyl group include a methylene group, an ethylene group, a propylene group, a butyene group, a pentylene group and a hexylene group.
$A^{F1}$ is preferably a C1 to C4 alkanediyl group, more preferably an ethylene group.

The aliphatic hydrocarbon group of $R^{F2}$ includes a straight or cyclic alkyl group, alicyclic group, and a group comprising the alkyl group and alicyclic group, which has a fluorine atom.

$R^{F2}$ is preferably fluorinated alkyl group and a fluorinated alicyclic group.

The fluorinated alkyl group has a fluorine atom by which a hydrogen atom of the alkyl group is replaced. Examples of the fluorinated alkyl group include difluoromethyl group, perfluoromethyl group 1,1-difluoroethyl group, 2,2-difluoroethyl group, 2,2,2-trifluoroethyl group, perfluoroethyl group, 1,1,2,2-tetrafluoropropyl group, 1,1,2,2,3,3-hexafluoropropyl group, a perfluoropeopyl group, 1-(trifluoromethyl)-1,1,2,2-tetrafluoroethyl group, 1,1,2,2-tetrafluorobutyl group, 1,1,2,2,3,3-hexafluorobutyl group, 1,1,2,2,3,3,4,4-octafluorobutyl group, a perfluorobutyl group, 1,1-bis(trifluoromethyl)-1,1,2,2-tetrafluoroethyl group, 2-(perfluoropropyl)ethyl group, 1,1,2,2,3,3,4,4-octafluopentyl group, perfluoropentyl group, decafluoropentyl group, 1,1-bis(trifluoromethyl)-2,2,3,3,3-pentafluoroethyl group, 2-(perfluorobutyl)ethyl group, 1,1,2,2,3,3,4,4,5,5-decafluorohexyl group, 1,1,2,2,3,3,4,4,5,5,6,6-dodecafluorohexyl group, (perfluoropentyl)methyl group, perfluorohexyl group.

The fluorinated alicyclic hydrocarbon group has a fluorine atom by which a hydrogen atom of the alicyclic hydrocarbon is replaced, which is typically a fluorinated cycloalkyl group such as perfluorocyclohexyl group, and perfluoroadamantyl group.

$R^{F2}$ is preferably a fluorinated alkyl group, more preferably C1-C6 fluorinated alkyl group.

When $A^{F1}$ is an ethylene group and $R^{F1}$ is a methyl group, examples of the structural unit represented by formula (FI) are shown as the following formulae.

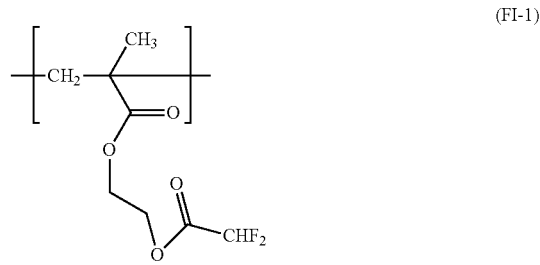

(FI-1)

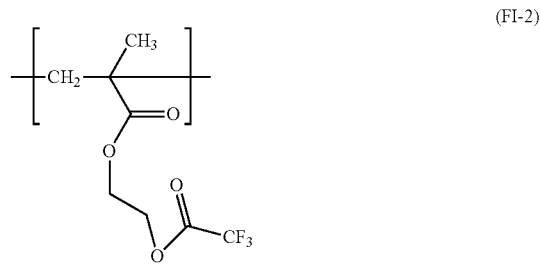

(FI-2)

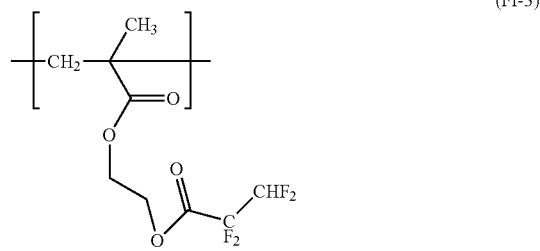

(FI-3)

(FI-4) 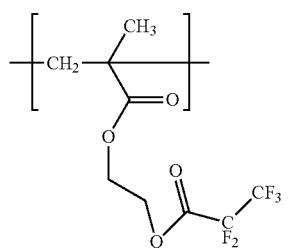

(FI-5) 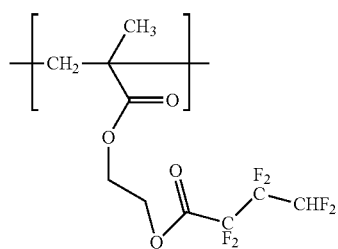

(FI-6) 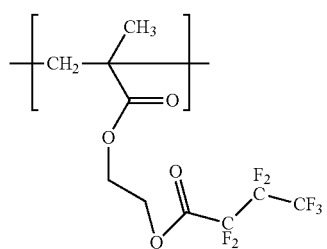

(FI-7) 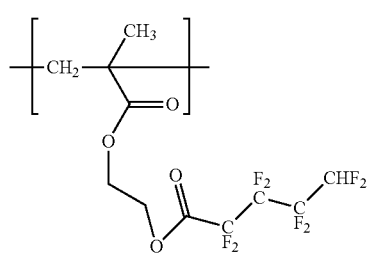

(FI-8) 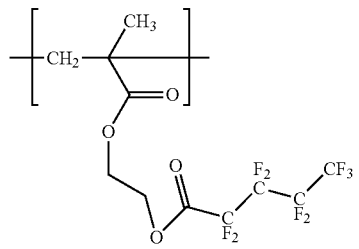

(FI-9) 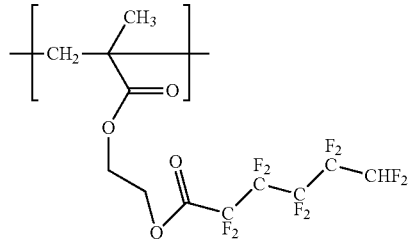

(FI-10) 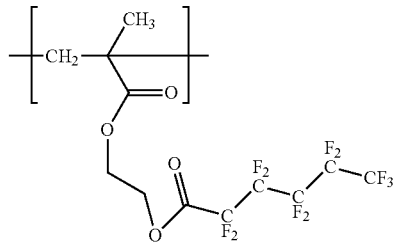

(FI-11) 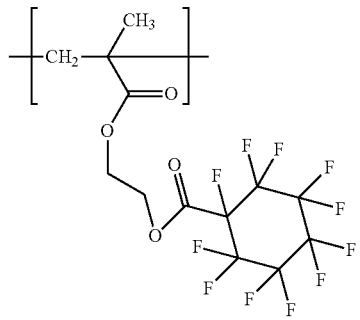

Examples of the structural unit represented by formula (FI) include those represented by formulae (FI-1) to (FI-11) wherein the methyl group corresponding to $R^{F1}$ has been replaced by a hydrogen atom.

The structural unit represented by formula (FI) is derived from the compound represented by formula (FI')

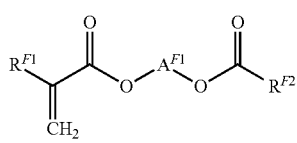
(FI')

wherein $R^{F1}$, $A^{F1}$ and $R^{F2}$ are defined as above.

The compound represented by formula (FI') can be prepared by reacting the compound represented by formula (FI'-1) with the compound represented by formula (FI'-2) in the presence of a basic compound in a solvent such as tetrahydrofuran, as represented by the following reaction formula.

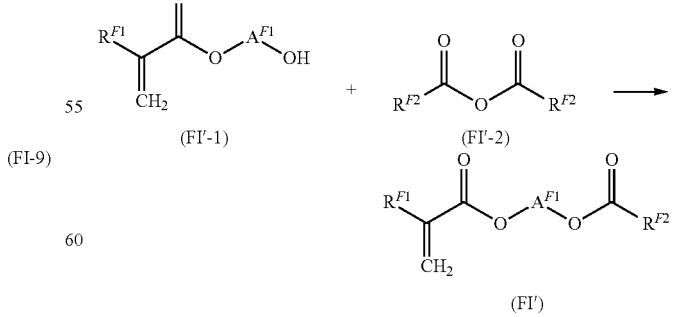

wherein $R^{F1}$, $A^{F1}$ and $R^{F2}$ are defined as above.

The compound represented by formula (FI'-1) is available on the market, which includes hydroxyethylmethacrylate.

The compound represented by formula (FI'-2) can be prepared by converting thereto a carboxylic acid corresponding to the compound depending on $R^{F2}$. The compound represented by formula (FI'-2) is also available on the market, which includes heptafluorobutyric acid anhydride.

The resin having the structural units represented by formula (FI) further has a structural unit other than one represented by formula (FI). However, the resin having a structural unit represented by formula (FI) has no acid-labile group.

Examples of the structural unit other than one represented by formula (FI) include one represented by the formula (a2) or the formula (a3), and one represented by the formula (FIII):

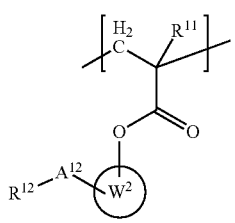

(FIII)

wherein $R^{11}$ represents a hydrogen atom or methyl group, the ring $W^2$ represents a C6-C10 aliphatic ring,
$A^{12}$ represents an oxygen atom, carbonyloxy group (*—CO—O—) or oxycarbonyl group (*—O—CO—) wherein * represents a binding site to ring $W^2$, and
$R^{12}$ represents a C1-C6 fluorinated alkyl group.

Examples of the fluorinated alkyl group represented by $R^{12}$ include difluoromethyl group, perfluoromethyl group-1, 1-difluoroethyl group, 2,2-difluoroethyl group, 2,2,2-trifluoroethyl group, perfluoroethyl group, 1,1,2,2-tetrafluoropropyl group, 1,1,2,2,3,3-hexafluoropropyl group, a perfluoropeopyl group, 1-(trifluoromethyl)-1,1,2,2-tetrafluoroethyl group, 1,1,2,2-tetrafluorobutyl group, 1,1,2,2,3,3-hexafluorobutyl group, 1,1,2,2,3,3,4,4-octafluorobutyl group, a perfluorobutyl group, 1,1-bis(trifluoromethyl)-1,1,2,2-tetrafluoroethyl group, 2-(perfluoropropyl)ethyl group, 1,1,2,2,3,3,4,4-octafluopentyl group, perfluoropentyl group, decafluoropentyl group, 1,1-bis(trifluoromethyl)-2,2,3,3,3-pentafluoroethyl group, 2-(perfluorobutyl)ethyl group, 1,1,2,2,3,3,4,4,5,5-decafluorohexyl group, 1,1,2,2,3,3,4,4,5,5,6,6-dodecafluorohexyl group, (perfluoropentyl)methyl group, and perfluorohexyl group.

$R^{12}$ preferably includes trifluoromethyl group, 2,2,2-trifluoroethyl group, perfluoroethyl group, a perfluoro-n-peopyl group, a perfluoro-n-butyl group, 1,1,2,2,3,3,4,4,5,5-decafluoro-n-hexyl group, The ring $W^2$ is preferably a saturated aliphatic ring free from a carbon-carbon double bond, which specifically includes a cyclohexane ring, a cycloheptane ring, a cyclooctane ring, a norbornane ring, an adamantane group and perhydronaphtarene ring, which preferably includes an adamantane group and a cyclohexane ring, and which more preferably includes an adamantane group.

The structural unit represented by the formula (FIII) is preferably one represented by one of the following formulae.

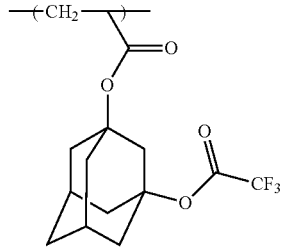
(FIII-1)

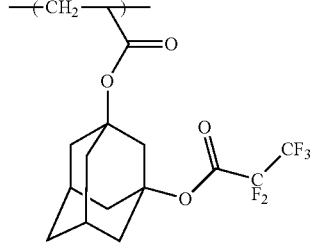
(FIII-2)

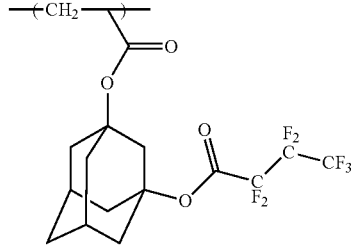
(FIII-3)

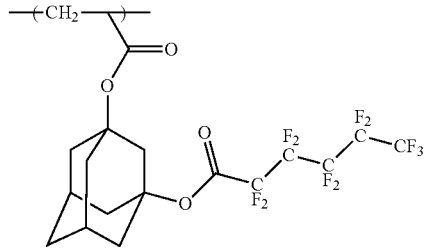
(FIII-4)

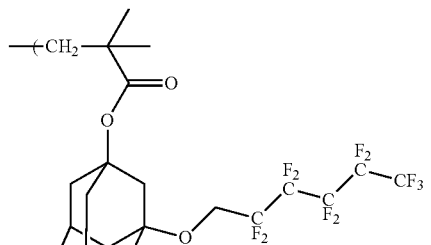
(FIII-5)

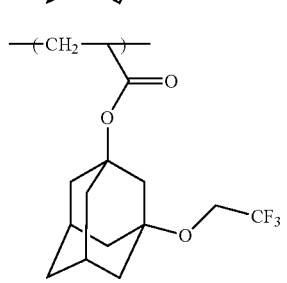
(FIII-6)

(FIII-7)

[Chemical structure of FIII-7: adamantane-based structure with CH2 repeating unit, ester linkages, and fluorinated side chain with CF3 group]

(FIII-8)

[Chemical structure of FIII-8: adamantane-based structure with CH2 repeating unit, ester linkages, and OCH2CF3 group]

Examples of the structural unit represented by formula (FIII) include those represented by formulae (FIII-1) to (FIII-8) wherein the methyl group corresponding to $R^{F1}$ has been replaced by a hydrogen atom.

The structural unit represented by formula (FIII) includes preferably one represented by formula (FIII) wherein $R^{11}$ is a hydrogen atom, more preferably those represented by formulae (FIII-1) to (FIII-8).

In the resin having a structural unit represented by the formula (FI), the structural unit represented by the formula (FI) accounts for preferably 5% by mole or more, more preferably 50 to 100% by mole, of the total mole amount of the structural units of the resin. In the resin having a structural unit represented by the formula (FI), the structural unit other than one represented by the formula (FI) is preferably one represented by the formula (FIII). The resin having a structural unit represented by the formula (FI) may consist of the structural unit represented by the formula (FI).

The resin having a structural unit represented by the formula (FI) can be obtained usually by polymerizing a compound from which the structural unit represented by formula (FI) is derived, as necessary with other compounds from which the structural unit other than one represented by formula (FI) is derived, such as a compound represented by formula (FIII) in a known manner. The content of the structural unit represented by formula (FI) can be controlled by adjusting a compound from which the structural unit represented by formula (FI) is derived, as necessary or other compounds from which the structural unit other than one represented by formula (FI).

The resin having a structural unit represented by the formula (FI) usually has 5,000 or more of the weight-average molecular weight, preferably 7,000 or more of the weight-average molecular weight. The resin usually has 80,000 or less of the weight-average molecular weight, preferably has 50,000 or less of the weight-average molecular weight.

The weight-average molecular weight can be measured with gel permeation chromatography (standard: polyethylene).

The photoresist compositions of the present invention can contain a basic compound as a quencher. The basic compound has the property that it can trap an acid, especially an acid generated from the acid generator by applying a radiation.

The basic compound is preferably a basic nitrogen-containing organic compound, and examples thereof include an amine compound and an ammonium salt. Amine compound includes an aliphatic amine and an aromatic amine. Examples of the aliphatic amine include a primary amine, a secondary amine and a tertiary amine. Examples of the aromatic amine include an aromatic amine in which aromatic ring has one or more amino groups such as aniline and a heteroaromatic amine such as pyridine.

The basic compounds include preferably a compound represented by the formulae (C1), (C2), (C3), (C4), (C5), (C6), (C7) and (C8), more preferably a compound represented by the formulae (C1-1).

(C1)

$$R^{c1}-N\begin{matrix}R^{c2}\\R^{c3}\end{matrix}$$

wherein $R^{c1}$, $R^{c2}$ and $R^{c3}$ independently represent a hydrogen atom, a C1-C6 alkyl group, a C5-C10 alicyclic hydrocarbon group or a C6-C10 aromatic hydrocarbon group, and the alkyl group and the alicyclic hydrocarbon group can have a substituent selected from the group consisting of a hydroxy group, an amino group and a C1-C6 alkoxy group, and the aromatic hydrocarbon group can have a substituent selected from the group consisting of C1-C6 alkyl groups, a C5-C10 alicyclic hydrocarbon group, a hydroxy group, an amino group, and a C1-C6 alkoxy group, (C1-1)

[Chemical structure: benzene ring with $(R^{c4})_{m3}$ substituent and $N(R^{c2})(R^{c3})$ group]

wherein $R^{c2}$ and $R^{c3}$ are defined as above, each of $R^{c4}$ independently represents a C1-C6 alkyl group, a C1-C6 alkoxy group, a C5-C10 alicyclic hydrocarbon group or a C6-C10 aromatic hydrocarbon group, and m3 represents an integer of 0 to 3, (C2)

$$R^{c5}-N\underset{\phantom{xx}}{\overset{\phantom{xx}}{\bigcirc}}N-R^{c6}$$

(C3)

$$R^{c7}-N\underset{\phantom{xx}}{\overset{\phantom{xx}}{\bigcirc}}O$$

(C4)

$$R^{c8}-N\underset{(R^{c9})_{n3}}{\overset{\phantom{xx}}{\bigcirc}}$$

wherein $R^{c5}$, $R^{c6}$, $R^{c7}$ and $R^{c8}$ are defined same as $R^{c1}$, each of $R^{c9}$ independently represents a C1-C6 alkyl group, a C3-C6 alicyclic group, or a C2-C6 alkanoyl group, and n3 represents an integer of 0 to 8,

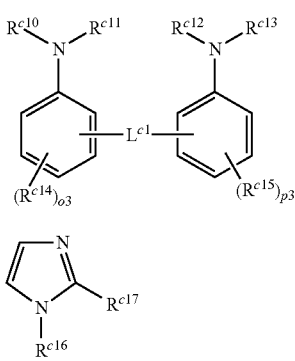

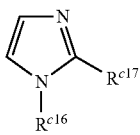

wherein each of $R^{c10}$, $R^{c11}$, $R^{c12}$, $R^{c13}$ and $R^{c16}$ is defined same as $R^{c1}$, each of $R^{c14}$, $R^{c15}$ and $R^{c17}$ is defined same as $R^{c4}$,
$L^{c1}$ represents a C1-C6 alkanediyl group, —CO—, —C(=NH)—, —S— or a combination thereof, and o3 and p3 respectively represent an integer of 0 to 3,

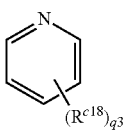

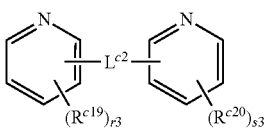

wherein each of $R^{c18}$, $R^{c19}$ and $R^{c20}$ is defined same as $R^{c4}$, $L^{c2}$ represents a single bond, a C1-C6 alkanediyl group, —CO—, —C(=NH)—, —S— or a combination thereof, and q3, r3 and p3 respectively represent an integer of 0 to 3.

Examples of the compound represented by the formula (C1) include 1-naphthylamine, 2-naphthylamine, aniline, diisopropylaniline, 2-methylaniline, 3-methylaniline, 4-methylaniline, 4-nitroaniline, N-methylaniline, N,N-dimethylaniline, diphenylamine, hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethydipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane and 4,4'-diamino-3,3'-diethyldiphenylmethane. Among them, preferred is diisopropylaniline and more preferred is 2,6-diisopropylaniline Examples of the compound represented by the formula (C2) include piperazine.

Examples of the compound represented by the formula (C3) include morpholine.

Examples of the compound represented by the formula (C4) include piperidine and hindered amine compounds having a piperidine skeleton as disclosed in JP 11-52575 A1.

Examples of the compound represented by the formula (C5) include 2,2'-methylenebisaniline.

Examples of the compound represented by the formula (C6) include imidazole and 4-methylimidazole.

Examples of the compound represented by the formula (C7) include pyridine and 4-methylpyridine.

Examples of the compound represented by the formula (C8) include di-2-pyridylketone, 1,2-di(2-pyridyl)ethane, 1,2-di(4-pyridyl)ethane, 1,3-di(4-pyridyl)propane, 1,2-bis(2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine, 2,2'-dipicolylamine and bipyridine.

Examples of the ammonium salt include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

The photoresist compositions of the present invention usually contain a solvent.

Examples of the solvent include a glycol ether ester such as ethyl cellosolve acetate, methyl cellosolve acetate and propylene glycol monomethyl ether acetate; an ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The photoresist compositions of the present invention can contain, if necessary, a small amount of various additives such as a sensitizer, a dissolution inhibitor, otherpolymers, a surfactant, a stabilizer and a dye as long as the effect of the present invention is not prevented.

The photoresist compositions of the present invention can usually be prepared by mixing, in a solvent, an acid generator containing the SALT (I), and a resin (A), and if necessary a basic compound, a resin having the structural unit represented by formula (FI) and/or additives at a suitable ratio for the composition, optionally followed by filtrating the mixture with a filter having 0.2 μm of a pore size.

The order of mixing these components is not limited to any specific order. The temperature at mixing the components is usually 10 to 40° C., which can be selected in view of the resin or the like.

The mixing time is usually 0.5 to 24 hours, which can be selected in view of the temperature. The means for mixing the components is not limited to specific one. The components can be mixed by being stirred.

The amounts of the components in the photoresist compositions can be adjusted by selecting the amount to be used for production of them.

The photoresist composition of the present invention usually contains 80% by weight or more of the resins based on sum of solid component. The photoresist composition of the present invention usually contains 99% by weight or less of the resins based on sum of solid component. In this specification, "solid component" means components other than solvent in the photoresist composition.

When the photoresist composition contains the resin having the structural unit represented by formula (FI), the content of the resin is usually 0.1 to 30 weight parts, preferably 1 to 25 weight parts, more preferably 5 to 10 weight parts relative to 100 weight parts of the resin (A).

The content of SALT (I) is preferably 0.1 part by weight or more, more preferably 1 part by weight or more, still more preferably 10 part by weight or more, and the content of SALT (I) is preferably 35 parts by weight or less, more preferably 30 parts by weight or less, still more preferably 25 parts by weight or less, per 100 parts by weight of the total solid components of the photoresist composition.

When the photoresist compositions contain the basic compound, the content thereof is usually 0.01 to 5%, preferably 0.01 to 3%, more preferably 0.01 to 1% by weight based on sum of solid component.

The amount of the solvent is usually 90% by weight or more, preferably 92% by weight or more preferably 94% by weight or more based on total amount of the photoresist composition of the present invention. The amount of the solvent is usually 99.9% by weight or less and preferably 99% by weight or less based on total amount of the photoresist composition of the present invention.

The photoresist compositions of the present invention are useful for a chemically amplified photoresist composition.

A photoresist pattern can be produced using the photoresist composition of the present invention by the following steps (1) to (5):

(1) a step of applying the photoresist composition of the present invention on a substrate,
(2) a step of forming a photoresist film by conducting drying,
(3) a step of exposing the photoresist film to radiation,
(4) a step of baking the exposed photoresist film, and
(5) a step of developing the baked photoresist film to form a photoresist pattern.

The applying of the photoresist composition on a substrate is usually conducted using a conventional apparatus such as spin coater. The photoresist composition is preferably filtrated with filter having 0.2 µm of a pore size before applying. Examples of the substrate include a silicon wafer or a quartz wafer on which a sensor, a circuit, a transistor or the like is formed. The substrate may be coated with a reflect-preventing layer such as one containing hexamethyldisilazane. For forming the reflect-preventing layer, such composition for organic reflect-preventing layer as available on the market can be used.

The photoresist film is usually formed by heating the coat layer with a heating apparatus such as hot plate or a decompressor, to thereby dry off the solvent. The heating temperature is preferably 50 to 200° C., and the operation pressure is preferably 1 to $1.0*10^5$ Pa. These conditions can be selected in view of the solvent.

The photoresist film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a F2 laser (wavelength: 157 nm), and a light source radiating harmonic laser light in a far UV region or a vacuum UV region by wavelength conversion of laser light from a solid laser light source (such as YAG or semiconductor laser). The exposure source may be electric beam or extremely ultraviolet (EUV).

Exposure through a mask makes the composition layer have exposed areas and unexposed area. At the exposed area, the acid generator contained in the component layer gives an acid due to exposure energy. The acid generated from the acid generator acts on an acid-labile group of the resin, so that the deprotection reaction proceeds, resulting that the resin shows hydrophilic. Therefore, the resin becomes soluble with an alkaline solution at exposed area of the composition layer. On the other hand, unexposed area of the composition layer remains insoluble or poorly soluble in an aqueous alkali solution even after exposure. The solubility for an aqueous alkali solution is much different between the exposed area and unexposed area.

The step of baking of the exposed photoresist film is so called post-exposure bake, which is conducted with heating means such as hot plates. The temperature of baking of the exposed photoresist film is preferably 50 to 200° C., and more preferably 70 to 150° C. The deprotection reaction further proceeds by post-exposure bake.

The development of the baked photoresist film is usually carried out with alkaline developer using a development apparatus. The development can be conducted by contacting the baked photoresist film into with an aqueous alkaline solution to thereby remove the film at exposed area from the substrate while remain the film at unexposed area, forming the photoresist pattern. The alkaline developer to be used may be any one of various alkaline aqueous solution used in the art. Generally, an aqueous solution of tetramethylammonium hydroxide or (2-hydroxyethyl)trimethylammonium hydroxide (commonly known as "choline") is often used.

After development, the photoresist pattern formed is preferably washed with ultrapure water, and the remained water on the photoresist pattern and the substrate is preferably removed.

The process of the present invention can provide a photoresist pattern with less Line width Roughness The photoresist composition of the present invention is suitable for ArF excimer laser lithography, KrF excimer laser lithography, EUV exposure lithography and EB (electron beam) lithography.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted.

The weight-average molecular weight of any material used in the following examples is a value found by gel permeation chromatography [Column: Three of TSKgel Multipore HXL-M with guard column, manufactured by TOSOH CORPORATION, Solvent: tetrahydrofuran, Flow rate: 1.0 mL/min., Detector: RI Detector, Column temperature: 40° C., Injection volume: 100 µL] using standard polystyrene as a standard reference material.

Structures of compounds were determined by mass spectrometry (Liquid Chromatography: 1100 Type, manufactured by AGILENT TECHNOLOGIES LTD., Mass Spectrometry: LC/MSD Type, manufactured by AGILENT TECHNOLOGIES LTD.). Hereinafter, the value of the peak in the mass spectrometry is referred to as "MASS".

Synthesis Example 1

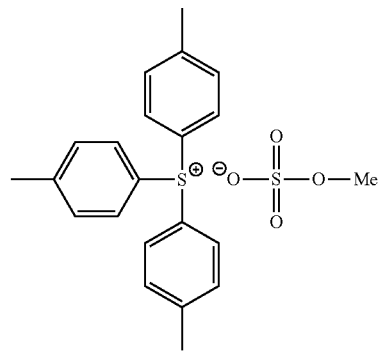

(I-A-c-1)

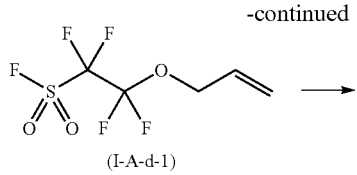

(I-A-d-1)

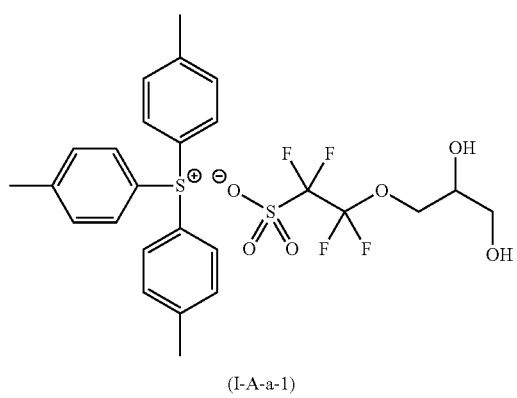

(I-A-b-1)

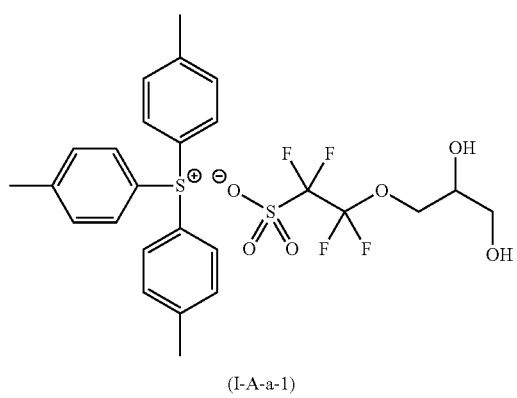

(I-A-a-1)

To a mixture of 20 parts of the compound represented by formula (I-A-c-1), 100 parts of chloroform and 20 parts of deionized water, a mixture of 10.2 parts of triethylamine and 12.11 parts of the compound represented by formula (I-A-d-1) was added and then stirred at room temperature for 4 hours. To the resulting reaction mixture, 120 parts of 5% aqueous oxalic acid solution was added thereto and extracted with chloroform, followed by being washed with deionized water. The extracted organic layer was concentrated by depressurization. To the obtained residue, the mixture of acetonitrile, 2-methoxy-2-methylpropane and n-heptane (acetonitrile/2-methoxy-2-methylpropane/n-heptane=1/4/4, weight ratio) was added and then stirred. The supernatant was removed therefrom and then the residue was dried to obtain 25.9 parts of salt represented by the formula (I-A-b-1).

To a mixture of 20.2 parts of the compound represented by formula (I-A-b-1) and 100 parts of chloroform, 9.16 parts of 50% aqueous solution of 4-methylmorpholine N-oxide and 0.64 parts of 4% aqueous solution of osmium tetraoxide were added. The resulting mixture was stirred at room temperature for 24 hours. To the resulting reaction mixture, 30 parts of 1% aqueous oxalic acid solution was added thereto and extracted with chloroform, followed by being washed with deionized water. The extracted organic layer was concentrated by depressurization. To the obtained residue, the mixture of acetonitrile, 2-methoxy-2-methylpropane and n-heptane (acetonitrile/2-methoxy-2-methylpropane/n-heptane=1/4/4, weight ratio) was added and then stirred. The supernatant was removed therefrom and then the residue was dried to obtain 21.95 parts of salt represented by the formula (I-A-a-1).

MASS(ESI(+)) Spectrum): M$^+$ 305.1 (C$_{21}$H$_{21}$S$^+$=305.1)

MASS(ESI(−)) Spectrum): M$^-$ 271.0 (C$_5$H$_7$F$_4$O$_6$S$^-$=271.0)

Example 1

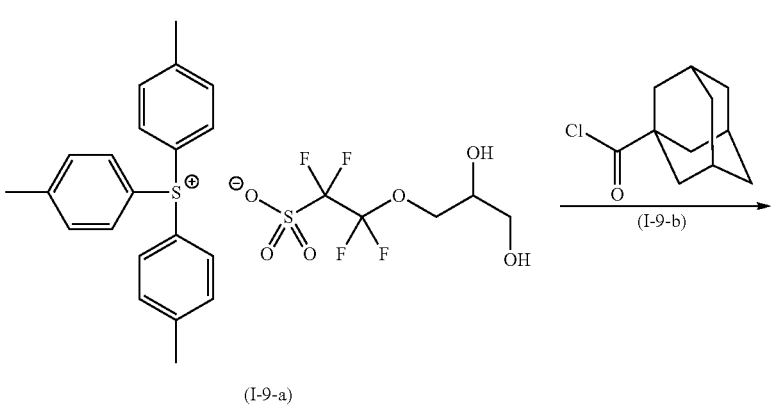

(I-9-a)

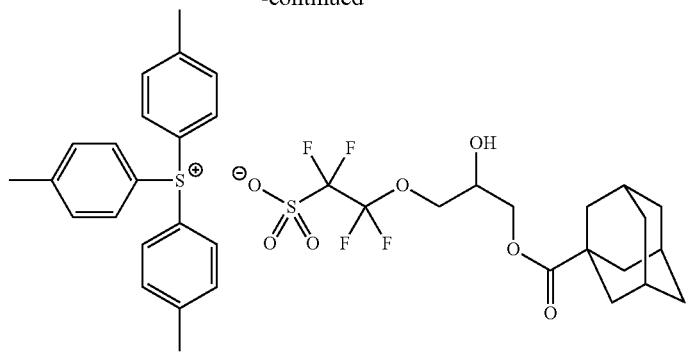

(I-9)

To a mixture of 1.7 parts of the compound represented by formula (I-9-a) and 24 parts of chloroform, 0.37 parts of N-methylpyrrolidine and 0.7 parts of the compound represented by formula (I-9-b) were added. The resulting mixture was stirred at room temperature for 4 hours. To the resulting reaction mixture, 33 parts of 1% aqueous oxalic acid solution was added thereto and extracted with chloroform, followed by being washed with deionized water. The extracted organic layer was concentrated by depressurization. To the obtained residue, the mixture of acetonitrile, 2-methoxy-2-methylpropane and n-heptane (acetonitrile/2-methoxy-2-methylpropane/n-heptane=1/4/4, weight ratio) was added and then stirred. The supernatant was removed therefrom and then the residue was dried to obtain 0.94 parts of salt represented by the formula (I-9).

MASS(ESI(+) Spectrum): $M^+$ 305.1 ($C_{21}H_{21}S^+$=305.1)
MASS(ESI(−) Spectrum): $M^-$ 433.1 ($C_{16}H_{21}F_4O_7S^-$=433.1)

Example 2

To a mixture of 1.5 parts of the compound represented by formula (I-12-a) and 12 parts of chloroform, 1.1 parts of triethylamine and 1.42 parts of the compound represented by formula (I-12-b) were added. The resulting mixture was stirred at room temperature for 4 hours. To the resulting reaction mixture, 72 parts of 1% aqueous oxalic acid solution was added thereto and extracted with chloroform, followed by being washed with deionized water. The extracted organic layer was concentrated by depressurization. To the obtained residue, the mixture of acetonitrile, 2-methoxy-2-methylpropane and n-heptane (acetonitrile/2-methoxy-2-methylpropane/n-heptane=1/4/4, weight ratio) was added and then stirred. The supernatant was removed therefrom and then the residue was dried to obtain 0.9 parts of salt represented by the formula (I-12).

MASS(ESI(+) Spectrum): $M^+$ 305.1 ($C_{21}H_{21}S^+$=305.1)
MASS(ESI(−) Spectrum): $M^-$ 494.1 ($C_{19}H_{27}F_4O_8S^-$=494.1)

Example 3

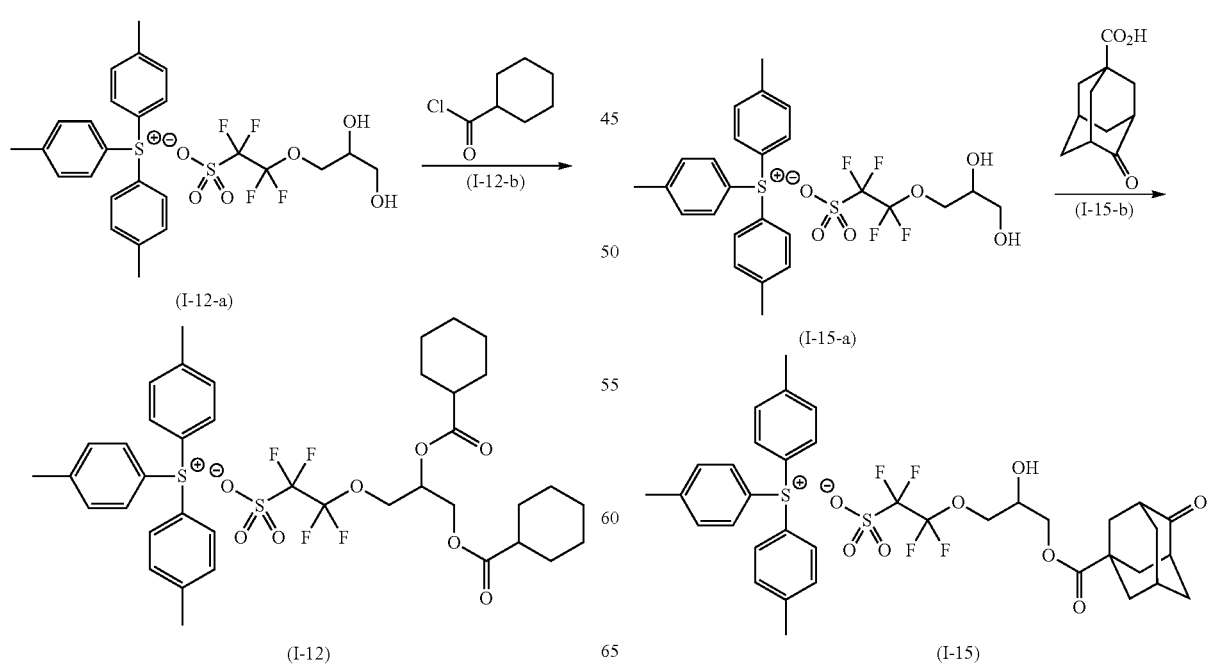

To a mixture of 7.12 parts of the compound represented by formula (I-15-b) and 28 parts of chloroform, 5.95 parts of 1,1'-carbonyldiimidazole was added and then stirred at room temperature for 3 hours. To the resulting mixture, 14.1 parts of the compound represented by formula (I-15-a) and 50 parts of chloroform were added and then stirred at room temperature for 1 hour.

To the resulting reaction mixture, potassium carbonate was added and then extracted with chloroform. The obtained organic layer was washed with deionized water, followed by concentrating it by depressurization. To the obtained residue, the mixture of acetonitrile, 2-methoxy-2-methylpropane and n-heptane (acetonitrile/2-methoxy-2-methylpropane/n-heptane=1/4/4, weight ratio) was added and then stirred. The supernatant was removed therefrom and then the residue was dried to obtain 12 parts of salt represented by the formula (I-15).

MASS(ESI(+) Spectrum): $M^+$ 305.1 ($C_{21}H_{21}S^+$=305.1)
MASS(ESI(−) Spectrum): $M^-$ 447.1 ($C_{16}H_{19}F_4O_8S^-$=447.1)

Example 4

To a mixture of 1.9 parts of the compound represented by formula (I-15-b) and 7.6 parts of chloroform, 1.59 parts of 1,1'-carbonyldiimidazole was added and then stirred at room temperature for 3 hours. To the resulting mixture, 4.9 parts of the compound represented by formula (I-15) and 7 parts of chloroform were added, and then stirred for 3 hours under distillation by heating. To the reaction mixture, potassium carbonate was added and extracted with chloroform.

The obtained organic layer was washed with deionized water, followed by concentrating it by depressurization. To the obtained residue, the mixture of acetonitrile, 2-methoxy-2-methylpropane and n-heptane (acetonitrile/2-methoxy-2-methylpropane/n-heptane=1/4/4, weight ratio) was added and then stirred. The supernatant was removed therefrom and then the residue was dried to obtain 5.9 parts of salt represented by the formula (I-18).

MASS(ESI(+) Spectrum): $M^+$ 305.1 ($C_{21}H_{21}S^+$=305.1)
MASS(ESI (−) Spectrum): $M^-$ 623.2 ($C_{27}H_{31}F_4O_{10}S^-$=623.2)

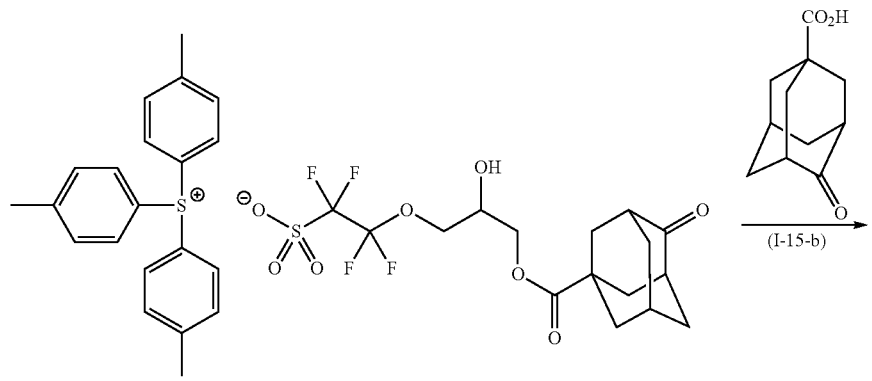

(I-15)

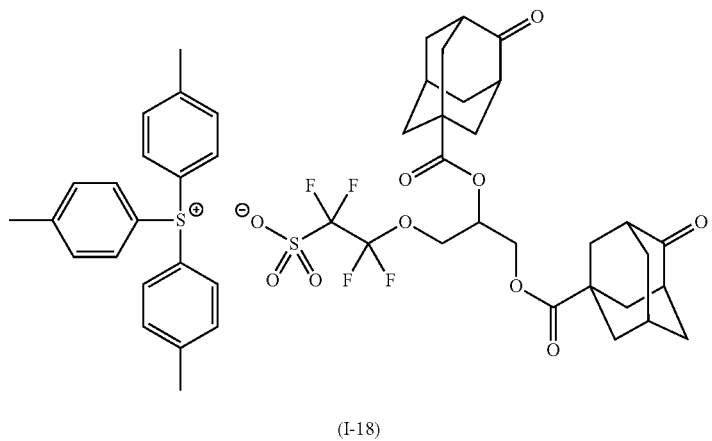

(I-18)

Example 5

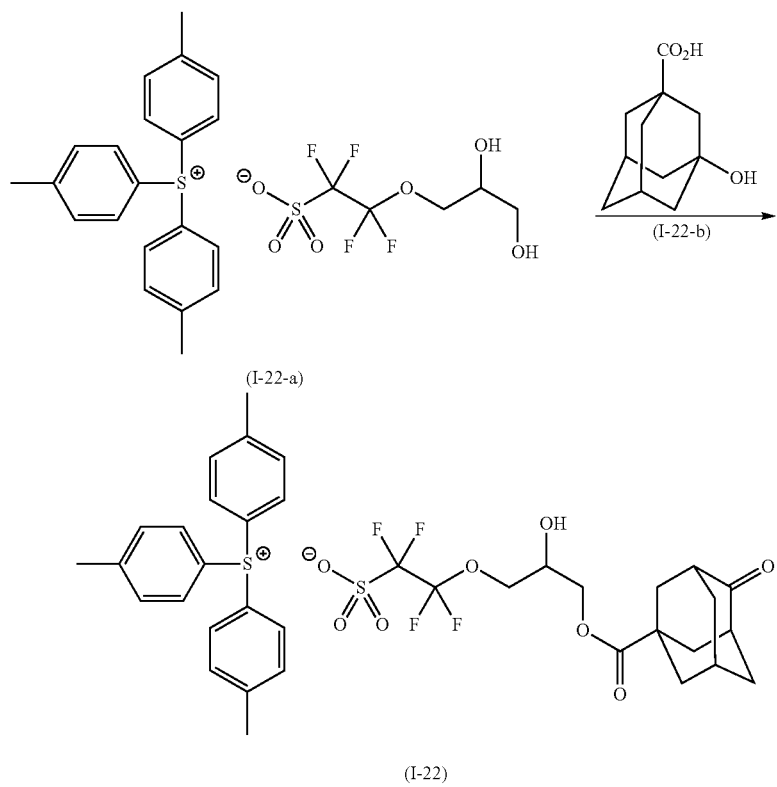

To a mixture of 2.19 parts of the compound represented by formula (I-22-b) and 8.8 parts of chloroform, 1.8 parts of 1,1'-carbonyldiimidazole was added and then stirred at room temperature for 3 hours. To the resulting mixture, 4.33 parts of the compound represented by formula (I-22-a) and 16 parts of chloroform were added, and then stirred at room temperature for 1 hour. To the reaction mixture potassium carbonate was added and extracted with chloroform. The obtained organic layer was washed with deionized water, followed by concentrating it by depressurization. To the obtained residue, the mixture of acetonitrile, 2-methoxy-2-methylpropane and n-heptane (acetonitrile/2-methoxy-2-methylpropane/n-heptane=1/4/4, weight ratio) was added and then stirred. The supernatant was removed therefrom and then the residue was dried to obtain 3.2 parts of salt represented by the formula (I-22).

MASS(ESI(+)) Spectrum): $M^+$ 305.1 ($C_{21}H_{21}S^+$=305.1)

MASS(ESI(-)) Spectrum): $M^-$ 449.1 ($C_{16}H_{21}F_4O_8 S^-$=449.1)

Example 6

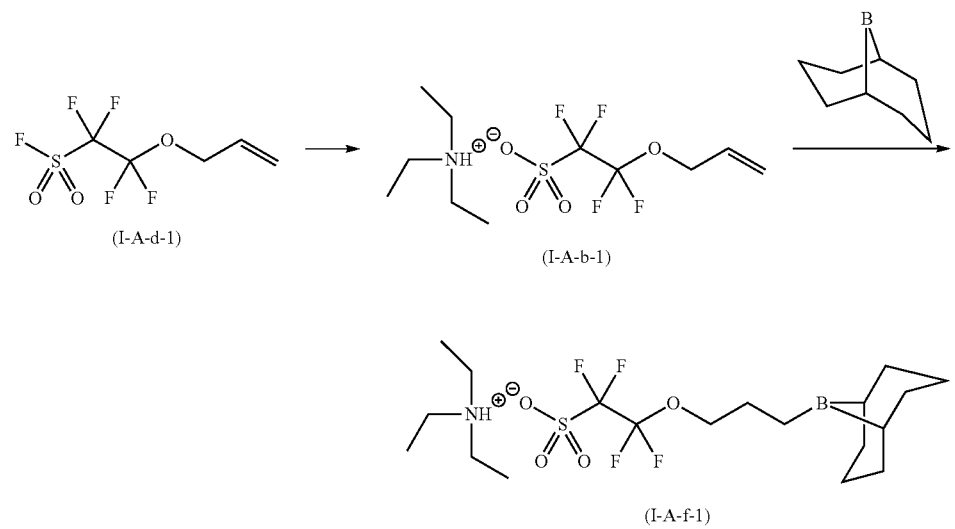

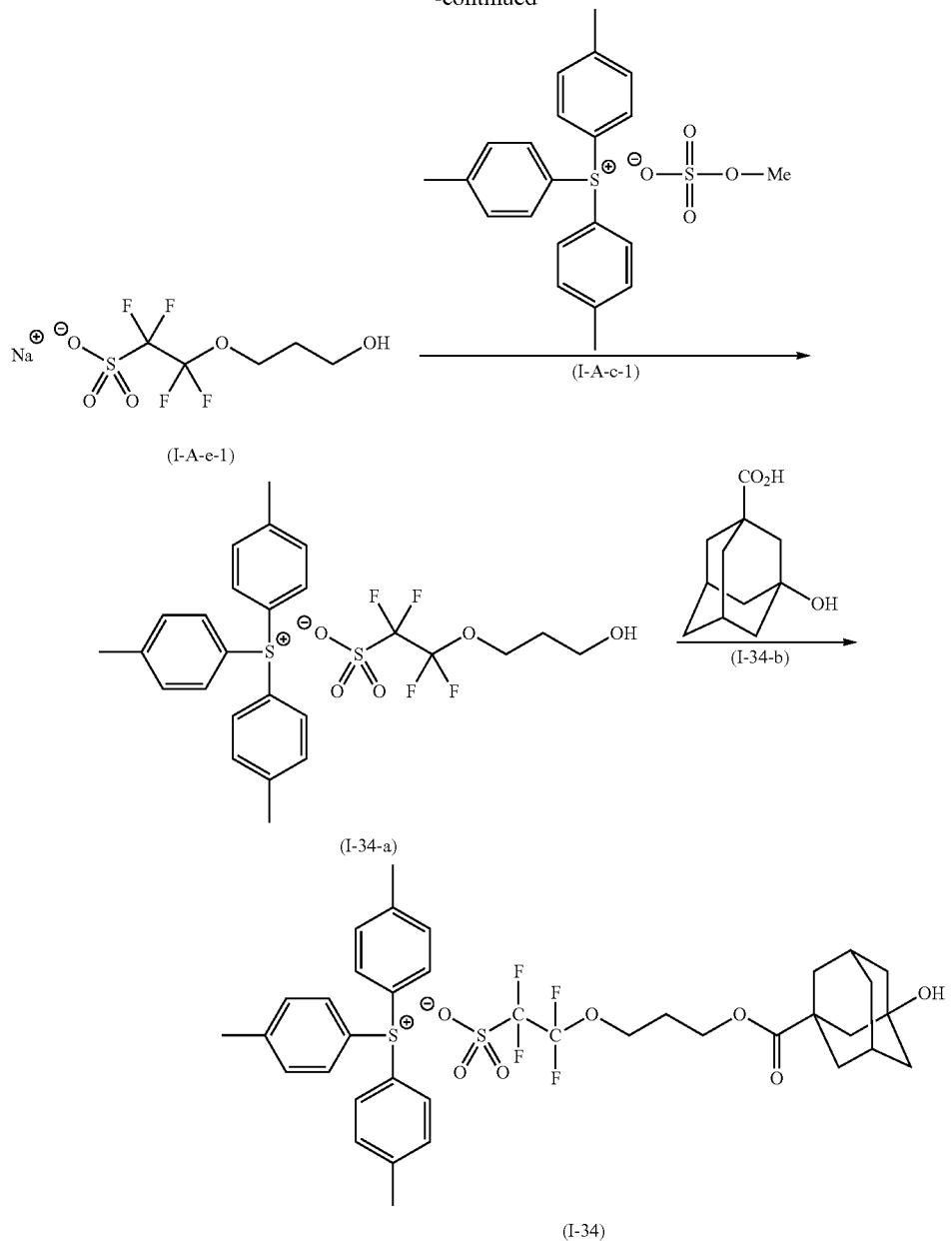

To a mixture of 10.2 parts of triethylamine, 100 parts of chloroform and 20 parts of deionized water, the compound represented by formula (I-A-d-1) was added, followed by stirring them at room temperature for 4 hours. Thereto, 120 parts of 5% aqueous oxalic acid solution was added and extracted with chloroform, followed by being washed with deionized water. The extracted organic layer was concentrated by depressurization to obtain 14 parts of the compound represented by formula (I-A-b-1). Into the mixture of 14 parts of the compound represented by formula (I-A-b-1) with 7 parts of tetrahydrofuran at 0° C., 99 parts of 5M tetrahydrofuran solution of 9-borabicyclo[3.3.1]nonane [9-BBN] was dropped, followed by stirring it at 0° C. for 1 hour. To the reaction mixture, 21 parts of 20% aqueous hydroxyperoxide solution was added and cooled to 0° C. To the reaction mixture, 67 parts of 20% aqueous hydroxyperoxide solution was added, followed by stirring it at room temperature for 18 hours. To the reaction mixture, sodium sulfite was added and then stirred for 1 hour. The reaction mixture was filtrated and then the mixture of 100 parts of chloroform and 8 parts of the compound represented by formula (I-A-d-1) was added to the obtained filtrates, followed by stirring it at room temperature for 5 hours. To the reaction mixture, 60 parts of 5% aqueous oxalic acid solution was added and extracted with chloroform, followed by being washed with deionized water. The extracted organic layer was concentrated by depressurization. The mixture of acetonitrile, 2-methoxy-2-methylpropane and n-heptane (acetonitrile/2-methoxy-2-methylpropane/n-heptane=1/4/4, weight ratio) was added thereto and stirred, and then the supernatant was removed therefrom, followed by drying the residue to obtain 13.2 parts of the salt represented by formula (I-34-a).

To a mixture of 1.69 parts of the compound represented by formula (I-34-b) and 6.7 parts of chloroform, 1.4 parts of 1,1'-carbonyldiimidazole was added and then stirred at room temperature for 3 hours. To the resulting mixture, 3.26 parts of the compound represented by formula (I-34-a) and 12 parts of chloroform were added, and then stirred at room temperature for 1 hour. To the reaction mixture, potassium carbonate was added and extracted with chloroform. The obtained organic layer was washed with deionized water, followed by concentrating it by depressurization. To the obtained residue, the mixture of acetonitrile, 2-methoxy-2-methylpropane and n-heptane (acetonitrile/2-methoxy-2-methylpropane/n-heptane=1/4/4, weight ratio) was added and then stirred. The supernatant was removed therefrom and then the residue was dried to obtain 2.6 parts of salt represented by the formula (I-34).

MASS(ESI(+) Spectrum): $M^+$ 305.1 ($C_{21}H_{21}S^+$=305.1)
MASS(ESI(-) Spectrum): $M^-$ 433.1 ($C_{16}H_{21}F_4O_8S^-$=433.1)

Example 7

To a mixture of 1.1 parts of the compound represented by formula (I-30-b) and 4.5 parts of chloroform, 0.94 parts of 1,1'-carbonyldiimidazole was added and then stirred at room temperature for 3 hours. To the resulting mixture, 2.2 parts of the compound represented by formula (I-34-a), which had been prepared as described in Example 6, and 8 parts of chloroform were added, and then stirred at room temperature for 1 hour. To the reaction mixture, potassium carbonate was added and extracted with chloroform. The obtained organic layer was washed with deionized water, followed by concentrating it by depressurization. To the obtained residue, the mixture of acetonitrile, 2-methoxy-2-methylpropane and n-heptane (acetonitrile/2-methoxy-2-methylpropane/n-heptane=1/4/4, weight ratio) was added and then stirred. The supernatant was removed therefrom and then the residue was dried to obtain 1.8 parts of salt represented by the formula (I-30).

MASS(ESI(+) Spectrum): $M^+$ 305.1 ($C_{21}H_{21}S^+$=305.1)
MASS(ESI(-) Spectrum): $M^-$ 431.1 ($C_{16}H_{21}F_4O_7S^-$=431.1)

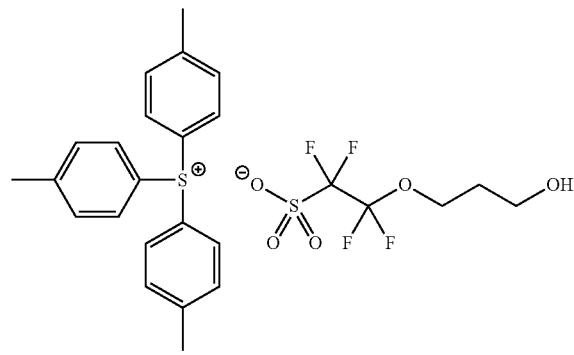

(I-34-a)

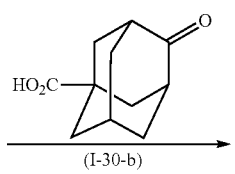

(I-30-b)

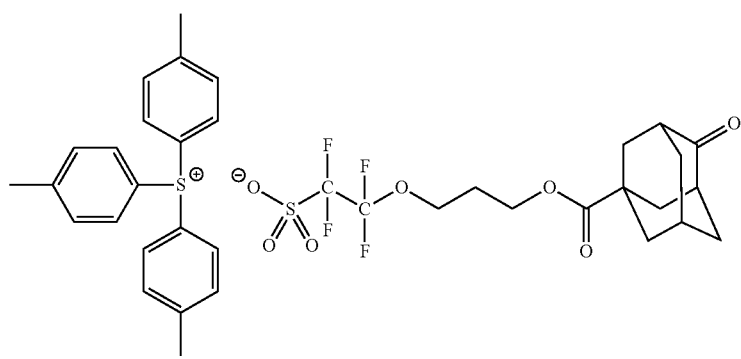

(I-30)

Example 8

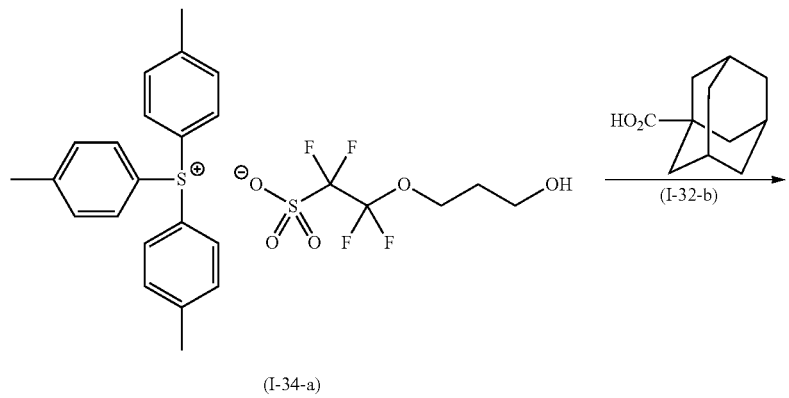

(I-34-a)

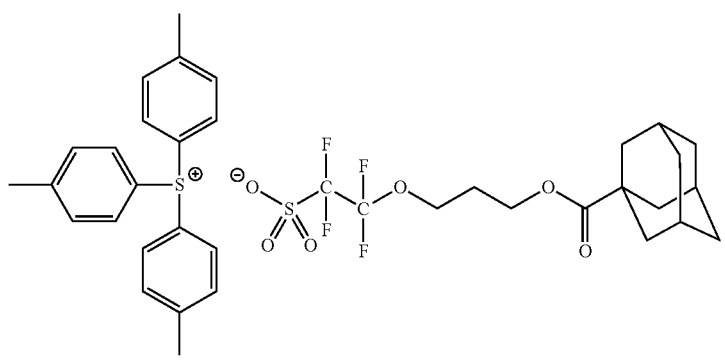

(I-32)

To a mixture of 1 part of the compound represented by formula (I-32-b) and 4.2 parts of chloroform, 0.94 parts of 1,1'-carbonyldiimidazole was added and then stirred at room temperature for 3 hours. To the resulting mixture, 2.2 parts of the compound represented by formula (I-34-a), which had been prepared as described in Example 6, and 8 parts of chloroform were added, and then stirred at room temperature for 1 hour. To the reaction mixture, potassium carbonate was added and extracted with chloroform. The obtained organic layer was washed with deionized water, followed by concentrating it by depressurization. To the obtained residue, the mixture of acetonitrile, 2-methoxy-2-methylpropane and n-heptane (acetonitrile/2-methoxy-2-methylpropane/n-heptane=1/4/4, weight ratio) was added and then stirred. The supernatant was removed therefrom and then the residue was dried to obtain 2 parts of salt represented by the formula (I-32).

MASS(ESI(+) Spectrum): $M^+$ 305.1 ($C_{21}H_{21}S^+$=305.1)

MASS(ESI(−) Spectrum): $M^-$ 417.1 ($C_{16}H_{21}F_4O_6S^-$=417.1)

Example 9

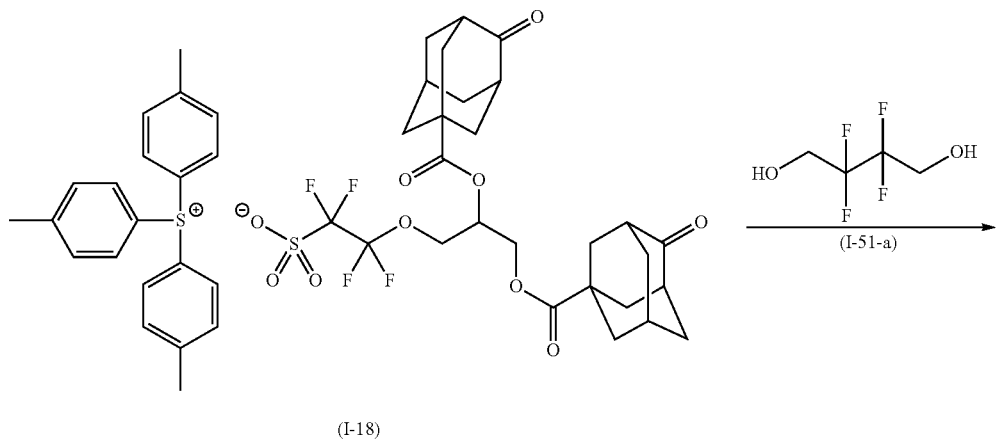

(I-18)

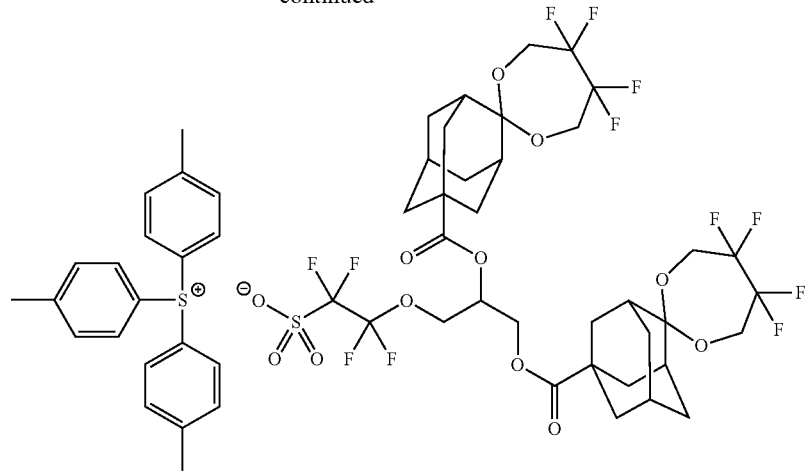

(I-51)

To a mixture of 2 part of the compound represented by formula (I-18) and 20 parts of chloroform, 0.9 parts of the compound represented by formula (I-51-a) and 0.018 parts of sulfuric acid were added and then stirred for 18 hours under distillation by heating. To the reaction mixture, potassium carbonate was added and extracted with chloroform. The obtained organic layer was washed with deionized water, followed by concentrating it by depressurization. To the obtained residue, the mixture of acetonitrile, 2-methoxy-2-methylpropane and n-heptane (acetonitrile/2-methoxy-2-methylpropane/n-heptane=1/5/10, weight ratio) was added and then stirred. The supernatant was removed therefrom and then the residue was dried to obtain 1.4 parts of salt represented by the formula (I-51).

MASS(ESI(+) Spectrum): $M^+$ 305.1 ($C_{21}H_{21}S^+$=305.1)

MASS(ESI(−) Spectrum): $M^-$ 943.3 ($C_{34}H_{47}F_{12}O_{12}S^-$=943.3)

Synthesis of Resin

The compounds used for producing resins were shown as follow.

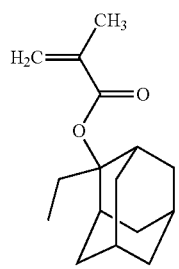

(M-1)

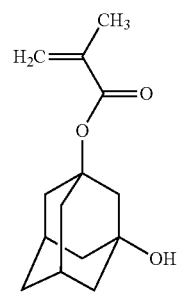

(M-2)

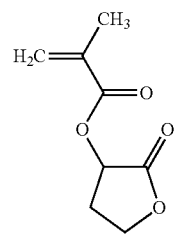

(M-3)

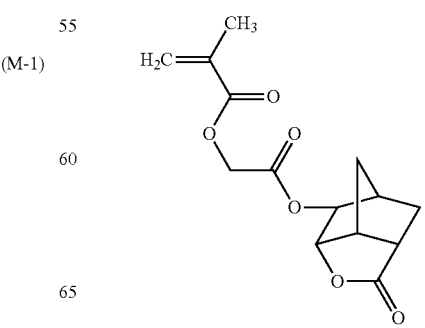

(M-6)

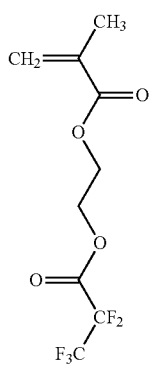

(MF-1)

Hereinafter, the compounds of the formulae are referred to as the symbols below the formulae. For example, the compound represented by formula (M-2) is referred to as "monomer (M-2)".

Resin Synthesis Example 1

To a reactor, 15 parts of monomer (M-1), 4.89 parts of monomer (M-2), 11.12 parts of monomer (M-6) and 8.81 parts of monomer (M-3) were fed, i.e., the monomers (M-1), (M-2), (M-6) and (M-3) were mixed in a molar ratio of 35/12/23/30 (monomer (M-1)/monomer (M-2)/monomer (M-6)/monomer (M-3)), and 1,4-dioxane was added thereto in the amount ratio of 1.5 times weight parts relative to the total parts of all monomers to prepare a mixture. To the mixture, azobisisobutyronitrile as an initiator in the molar ratio of azobisisobutyronitrile/all monomers=1/100 and azobis(2,4-dimethylvaleronitrile) as an initiator in the molar ratio of azobis(2,4-dimethylvaleronitrile)/all monomers=3/100 were added, and the resulting reaction mixture was heated at around 77° C. for about 5 hours.

The reaction mixture obtained was poured into a large amount of a mixture of methanol and water (weight ratio=4/1) to cause precipitation. This operation was conducted 3 times for purification. As a result, a resin having a weight-average molecular weight of about $8.1 \times 10^3$ was obtained in a yield of 78%. This resin is called as resin A1. Resin A1 had the following structural units.

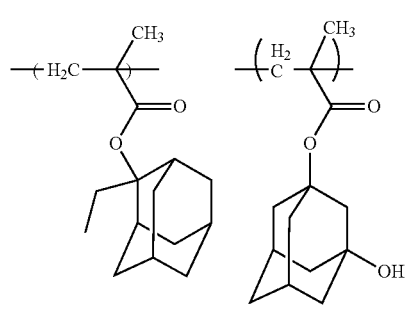

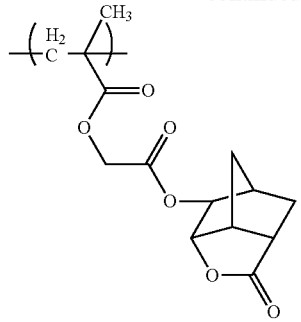

Resin Synthesis Example 2

To monomer (MF-1), 1,4-dioxane was added in the amount ratio of 1.5 times weight parts relative to the total parts of all monomer to prepare a mixture. To the mixture, azobisisobutyronitrile as an initiator in the molar ratio of azobisisobutyronitrile/all monomers=0.7/100 and azobis(2,4-dimethylvaleronitrile) as an initiator in the molar ratio of azobis(2,4-dimethylvaleronitrile)/all monomers=2.1/100 were added, and the obtained mixture was heated at 75° C. for about 5 hours. The reaction mixture obtained was poured into a large amount of a mixture of methanol and water (weight ratio=4/1) to cause precipitation. The precipitate was collected by filtration and then, was dissolved in 1,4-dioxane followed by poured the resultant solution into a large amount of a mixture of methanol and water to cause precipitation. This operation was conducted twice for purification. As a result, a resin having a weight-average molecular weight of about $1.8 \times 10^4$ was obtained in a yield of 77%. This resin is called as resin FI.

Resin FI had the following structural unit.

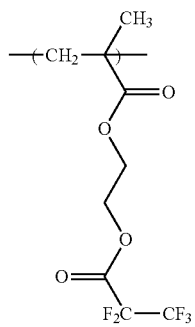

Examples 10 to 18 and Comparative Example 1

Preparation of Photoresist Composition

The following components were mixed and dissolved, further, filtrated through a fluorine resin filter having pore diameter of 0.2 μm, to prepare photoresist compositions shown in Table 1.

<Resin (A)>
Resin A1
<Resin (FI)>
Resin FI

<Acid Generator>
B1: The compound represented by formula (B1-6)
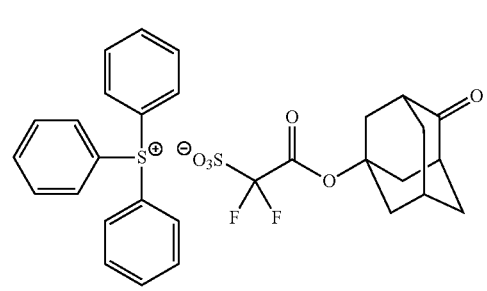
(B1-6)
<Salt (I)>
I-9: The compound represented by formula (I-9)
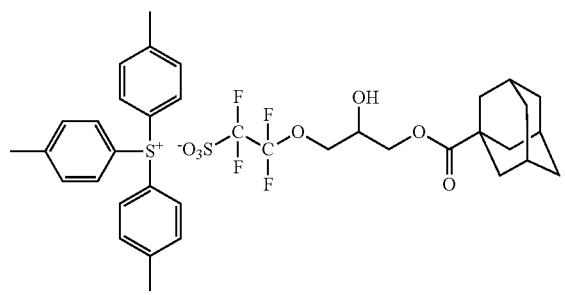
(I-9)
I-12: The compound represented by formula (I-12)
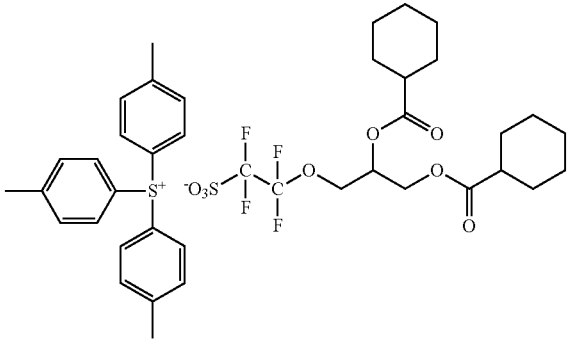
(I-12)
I-15: The compound represented by formula (I-15)
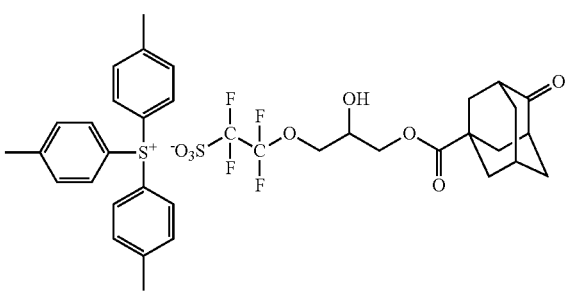
(I-15)
I-18: The compound represented by formula (I-18)
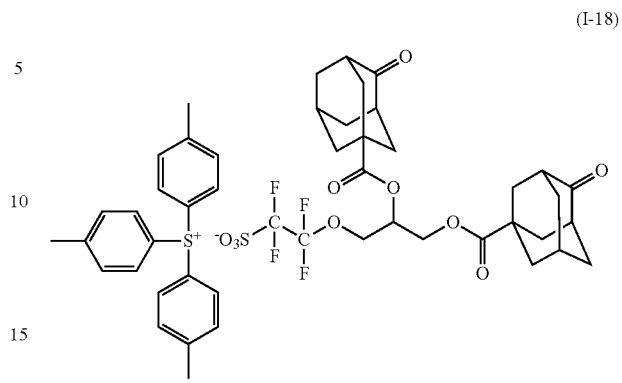
(I-18)
I-22 The compound represented by formula (I-22)
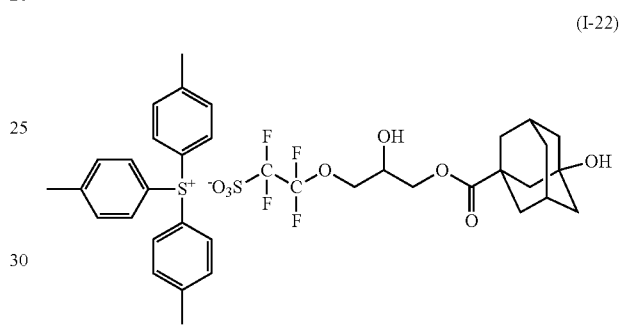
(I-22)
I-30: The compound represented by formula (I-30)
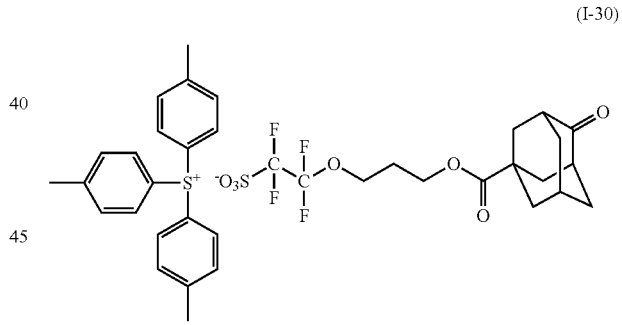
(I-30)
I-32: The compound represented by formula (I-32)
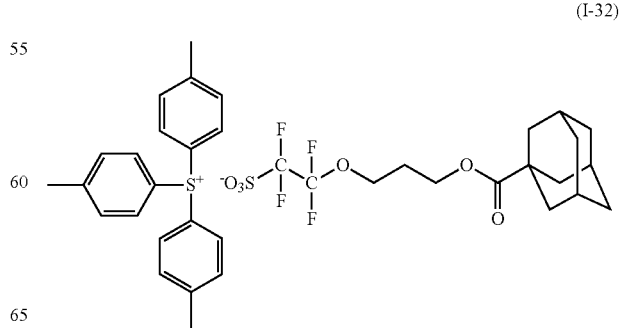
(I-32)

I-34: The compound represented by formula (I-34)

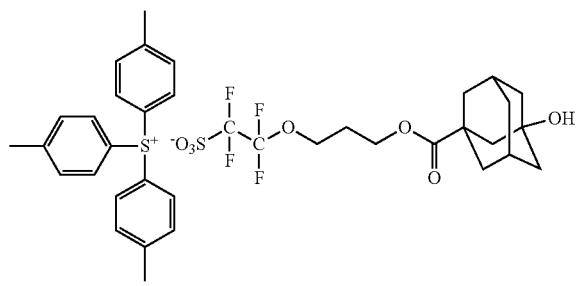

I-51: The compound represented by formula (I-51)

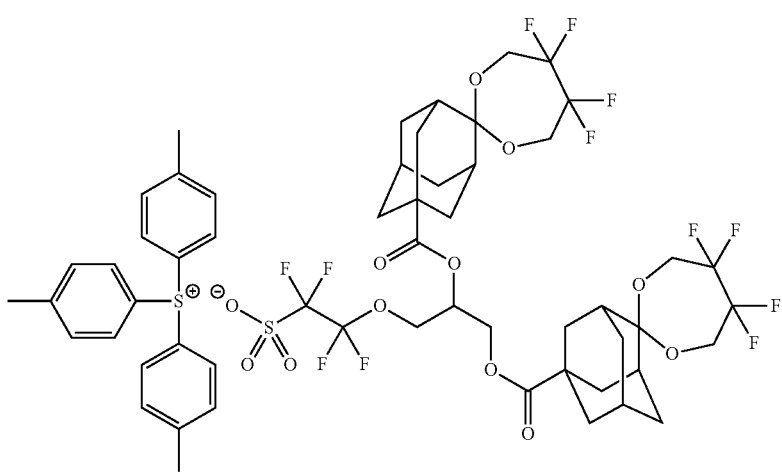

<Quencher>
Basic compound C1: 2,6-diisopropylaniline
<Solvent>

| | |
|---|---|
| propylene glycol monomethyl ether acetate | 270 parts |
| propylene glycol monomethyl ether | 20 parts |
| γ-butyrolactone | 3.5 parts |
| 2-heptane | 20 parts |

(Evaluation of CDU)

Silicon wafers (12 inches) were each coated with "AR-26N-510", which is an organic anti-reflective coating composition available from Rohm and Hass, and then baked at 205° C. for 60 seconds, to form a 48 nm-thick organic anti-reflective coating. Furthermore, the resulting coats were each coated with "XB-080957CA", which is an organic anti-reflective coating composition available from Rohm and Hass, and then baked at 205° C. for 60 seconds, to form a 40 nm-thick organic anti-reflective coating. The total thickness of the anti-reflective coatings was 88 nm.

Each of the photoresist compositions prepared as above was spin-coated over the anti-reflective coating so that the thickness of the resulting film became 90 nm after drying. The silicon wafers thus coated with the respective photoresist compositions were each prebaked on a direct hotplate at a temperature at 100° C. for 50 seconds. Using an ArF excimer stepper for immersion exposure ("XT: 1900Gi" manufactured by ASML, NA=1.3, Dispole 35, σ out/in =0.97/0.82, Y polarization), each wafer thus formed with the respective resist film was subjected to line and space pattern exposure with the exposure quantity being varied stepwise. At this exposure, a mask which had line and space pattern of 42 nm and a single dummy pattern of 40 nm set at the corner of the line and space pattern was used. Ultra pure water was used for immersion solvent.

TABLE 1

| | Resin (A) (Parts) | Resin (FI) (Parts) | Acid generator (Parts) | Salt (I) (Parts) | Basic compound (C) (Parts) | Solvent (D) (Parts) |
|---|---|---|---|---|---|---|
| Ex. 10 | A1 = 10 | FI = 0.7 | — | I-9 = 1 | C1 = 0.1 | D1 |
| Ex. 11 | A1 = 10 | FI = 0.7 | — | I-12 = 1 | C1 = 0.1 | D1 |
| Ex. 12 | A1 = 10 | FI = 0.7 | — | I-15 = 1 | C1 = 0.1 | D1 |
| Ex. 13 | A1 = 10 | FI = 0.7 | — | I-18 = 1.26 | C1 = 0.1 | D1 |
| Ex. 14 | A1 = 10 | FI = 0.7 | — | I-22 = 1 | C1 = 0.1 | D1 |
| Ex. 15 | A1 = 10 | FI = 0.7 | — | I-30 = 1 | C1 = 0.1 | D1 |
| Ex. 16 | A1 = 10 | FI = 0.7 | — | I-32 = 1 | C1 = 0.1 | D1 |
| Ex. 17 | A1 = 10 | FI = 0.7 | — | I-34 = 1 | C1 = 0.1 | D1 |
| Ex. 18 | A1 = 10 | FI = 0.7 | — | I-51 = 1 | C1 = 0.1 | D1 |
| Compar. Ex. 1 | A1 = 10 | FI = 0.7 | B1 = 1.00 | — | C1 = 0.1 | D1 |

After the exposure, each wafer was subjected to post-exposure baking on a hotplate at a temperature at 95° C. for 50 seconds and then to paddle development for 60 seconds with an aqueous solution of 2.38 wt % tetramethylammonium hydroxide.

Each of patterns developed on the organic anti-reflective coating substrate after the development was observed with a scanning electron microscope.

Effective Sensitivity (ES) was expressed as the amount of exposure that the line width of the line and space pattern of 42 nm became 1:1 after exposure through line and space pattern mask.

Evaluation of Pattern

The line and space pattern of 42 nm on the obtained film was observed with a running electron microscope. The pattern whose top and bottom are rectangular shape as shown in FIG. 1 (a) was determined as ◯. The pattern whose top and bottom are a round shape as shown in FIG. 1 (b) was determined as x. The results are shown in Table 2.

Evaluation of Optical Proximity Correction

The dummy pattern of 40 nm on the obtained film was observed with a scanning electron microscope.

The case where the dummy pattern was not existed on the film was determined as ◯. The case where the dummy pattern was existed partly or totally on the film was determined as x.

The results are shown in Table 2.

TABLE 2

|  | Shape | Dummy pattern |
|---|---|---|
| Ex. 10 | ◯ | ◯ |
| Ex. 11 | ◯ | ◯ |
| Ex. 12 | ◯ | ◯ |
| Ex. 13 | ◯ | ◯ |
| Ex. 14 | ◯ | ◯ |
| Ex. 15 | ◯ | ◯ |
| Ex. 16 | ◯ | ◯ |
| Ex. 17 | ◯ | ◯ |
| Ex. 18 | ◯ | ◯ |
| Compar. Ex. 1 | ◯ | X |

Since the photoresist composition of the present invention comprises a salt of the present invention, the photoresist composition can provide a photoresist pattern which is accurate, and which is free from a dummy pattern used for optical proximity correction even in case of conducting optical proximity correction with a dummy pattern, as apparent from the above-mentioned examples. The salt and the photoresist pattern of the present invention are suitable for semiconductor microfabrication employing lithography process.

What is claimed is:

1. A photoresist composition, which comprises a salt represented by formula (I):

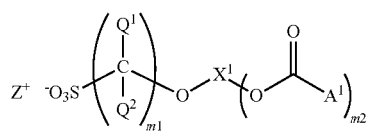

(I)

wherein $Q^1$ and $Q^2$ each independently represent a fluorine atom or a C1-C6 perfluoroalkyl group, $A^1$ represents a C3-C30 alicyclic hydrocarbon group in which a hydrogen atom may be replaced by a hydroxy group or a halogen group and in which a methylene group may be replaced by an oxygen atom, a sulfonyl group or a carbonyl group, $X^1$ represents a C1-C10 aliphatic hydrocarbon group where a hydrogen atom may be replaced by a hydroxy group, $m^1$ and $m^2$ independently each represent an integer of 1 to 4, and $Z^+$ represents an organic cation, a resin which is hardly soluble or insoluble but soluble in an aqueous alkali solution by action of an acid, and a resin having a structural unit represented by formula (F1):

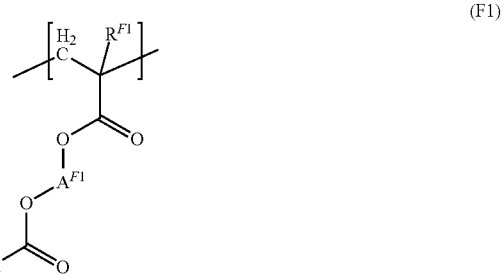

(F1)

wherein $R^{F1}$ represents a hydrogen atom or a methyl group, $A^{F1}$ represents a C1-C6 alkanediyl group, and $R^{F2}$ represents a C1-C10 hydrocarbon group having a fluorine atom.

2. A process for producing a photoresist pattern comprising the following steps (1) to (5):

(1) a step of applying the photoresist composition according to claim 1 on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

3. The photoresist composition according to claim 1, wherein $A^1$ represents a C3-C30 alicyclic hydrocarbon group in which a hydrogen atom may be replaced by a hydroxy group and in which a methylene group may be replaced by an oxygen atom, a sulfonyl group or a carbonyl group.

4. The photoresist composition according to claim 1, wherein $X^1$ is a C1-C5 aliphatic hydrocarbon group.

5. The photoresist composition according to claim 1, wherein $X^1$ is a C2-C5 aliphatic hydrocarbon group.

6. The photoresist composition according to claim 1, wherein $m^1$ is 2.

7. The photoresist composition according to claim 1, wherein $Z^+$ is an organic cation represented by formula (b2-1-1):

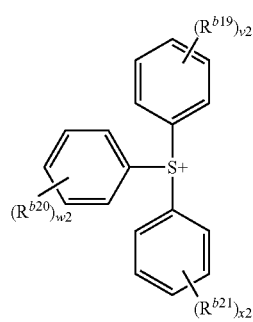

(b2-1-1)

wherein $R^{b19}$, $R^{b20}$ and $R^{b21}$ are independently in each occurrence a halogen atom, a hydroxy group, a C1-C18 alkyl group, a C3-C18 alicyclic hydrocarbon group, or a C1-C12 alkoxy group, and v2, w2 and x2 independently each represent an integer of 0 to 5.

8. The photoresist composition according to claim 7, wherein $R^{b19}$, $R^{b20}$ and $R^{b21}$ are a methyl group.

9. The photoresist composition according to claim 1, wherein $m^2$ is 2.

* * * * *